(12) United States Patent
Kazlausky et al.

(10) Patent No.: US 6,582,380 B2
(45) Date of Patent: Jun. 24, 2003

(54) SYSTEM AND METHOD OF MONITORING AND MODIFYING HUMAN ACTIVITY-BASED BEHAVIOR

(75) Inventors: Thomas Kazlausky, Glendale, NY (US); William Gruen, Cliffside Park, NJ (US); Warren W. Tryon, Briarcliff Manor, NY (US)

(73) Assignee: Ambulatory Monitoring, Inc., Ardsley, NY (US)

( * ) Notice: Subject to any disclaimer, the term of this patent is extended or adjusted under 35 U.S.C. 154(b) by 135 days.

(21) Appl. No.: 09/768,944

(22) Filed: Jan. 24, 2001

(65) Prior Publication Data

US 2001/0029319 A1 Oct. 11, 2001

Related U.S. Application Data

(60) Provisional application No. 60/177,778, filed on Jan. 24, 2000.

(51) Int. Cl.[7] ................................. A61B 5/103
(52) U.S. Cl. ....................................... 600/595
(58) Field of Search ................... 600/587–595, 600/300, 301; 482/18

(56) References Cited

U.S. PATENT DOCUMENTS

| | | | |
|---|---|---|---|
| 3,717,857 A | 2/1973 | Evans | 340/177 R |
| 4,112,926 A | 9/1978 | Schulman et al. | |
| 4,309,509 A | 1/1982 | Myers | |
| 4,353,375 A | 10/1982 | Colburn et al. | |
| 5,197,489 A | 3/1993 | Conlan | |
| 5,573,013 A | 11/1996 | Conlan | |
| 5,749,372 A | 5/1998 | Allen et al. | |
| 5,762,072 A | 6/1998 | Conlan et al. | |
| 6,032,530 A | 3/2000 | Hock | 73/379.01 |

OTHER PUBLICATIONS

Jerome I. Schulman et al., Instructions, Feedback, and Reinforcement in Reducing Activity Levels in the Classroom, Journal of Applied Behavior Analysis 1979, 12. 441–447, No. 3 (Fall 1979).

Jerome I. Schulman et al., The Biomotometer: A New (List continued on next page.)

*Primary Examiner*—Max F. Hindenburg
*Assistant Examiner*—Pamela Wingood
(74) *Attorney, Agent, or Firm*—Cohen, Pontani, Lieberman & Pavane

(57) ABSTRACT

A system and method for monitoring the activity level of one or more individuals and modifying the behavior of those individuals based on feedback from the activity level monitoring is disclosed. When applying the system and method to hyperactive children in a classroom environment, an activity monitor is attached to each hyperactive child. The activity monitor determines the intensity of the subject's activity at the end of each epoch (approximately every 5 seconds), stores the determined intensity, and compares the determined intensity to an epoch threshold. If the determined intensity exceeds the epoch threshold, the hyperactive child is given vibrotactile feedback by the attached activity monitor. The length of time that the vibrotactile feedback is applied is proportional to the amount the determined epoch intensity exceeds the epoch threshold. When the hyperactive child presses a button on the activity monitor to thereby request session feedback, the session intensity is compared to two different session thresholds, and one of three LEDs on the activity monitor is lit up, depending on where the session intensity is in comparison to the two session thresholds. A base station, either a simple hand-held device or a more complicated desk-top device, is under the control of the teacher and has a wireless communication link with the activity monitors so that information may be downloaded and the activity monitors may be controlled.

62 Claims, 13 Drawing Sheets

OTHER PUBLICATIONS

Device for the Measurement and Remediation of Hyperactivity, Child Development, 1977, 48. 1152–1154, ©1977 by the Society for Research in Child Development, Inc.

Jerome I. Schulman, et al., Modification of Activity Level Through Biofeedback and Operant Conditioning, Journal of Applied Behavior Analysis, 1978, 11. 145–152, No. 1, Spring 1978.

Steve Levinson Ph.D., Motiv Aider® System 2000.

Laurence D. Becker. Ph.D., WatchMinder™—A Training Reminder System for Persons with Attention Discorders.

Michael Gordon, Ph.D., Attention Training System Starter Package 2000.

Sensor Type and Orientation, Sensor Calibration & Reproducibility.

ActiTrac Method.

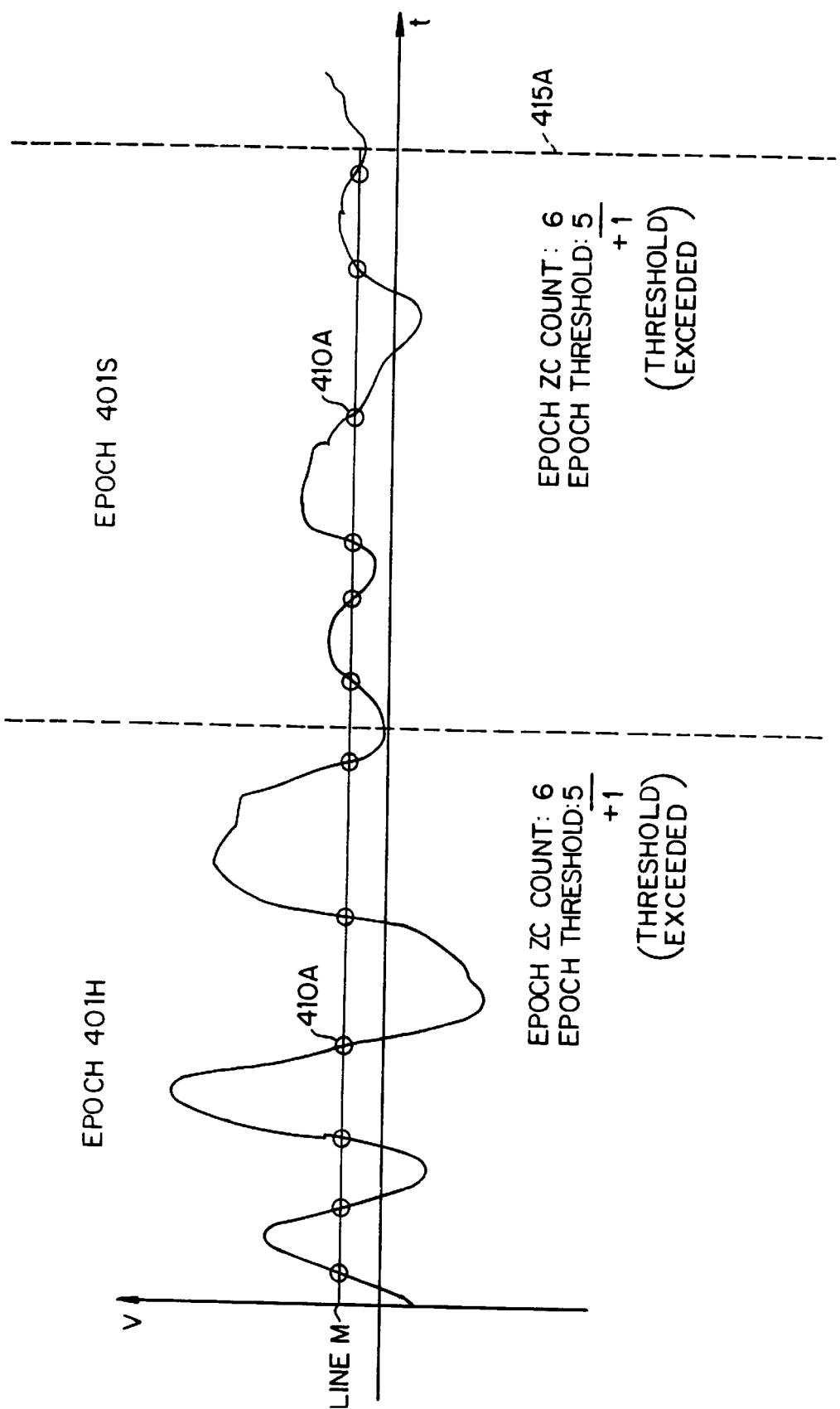

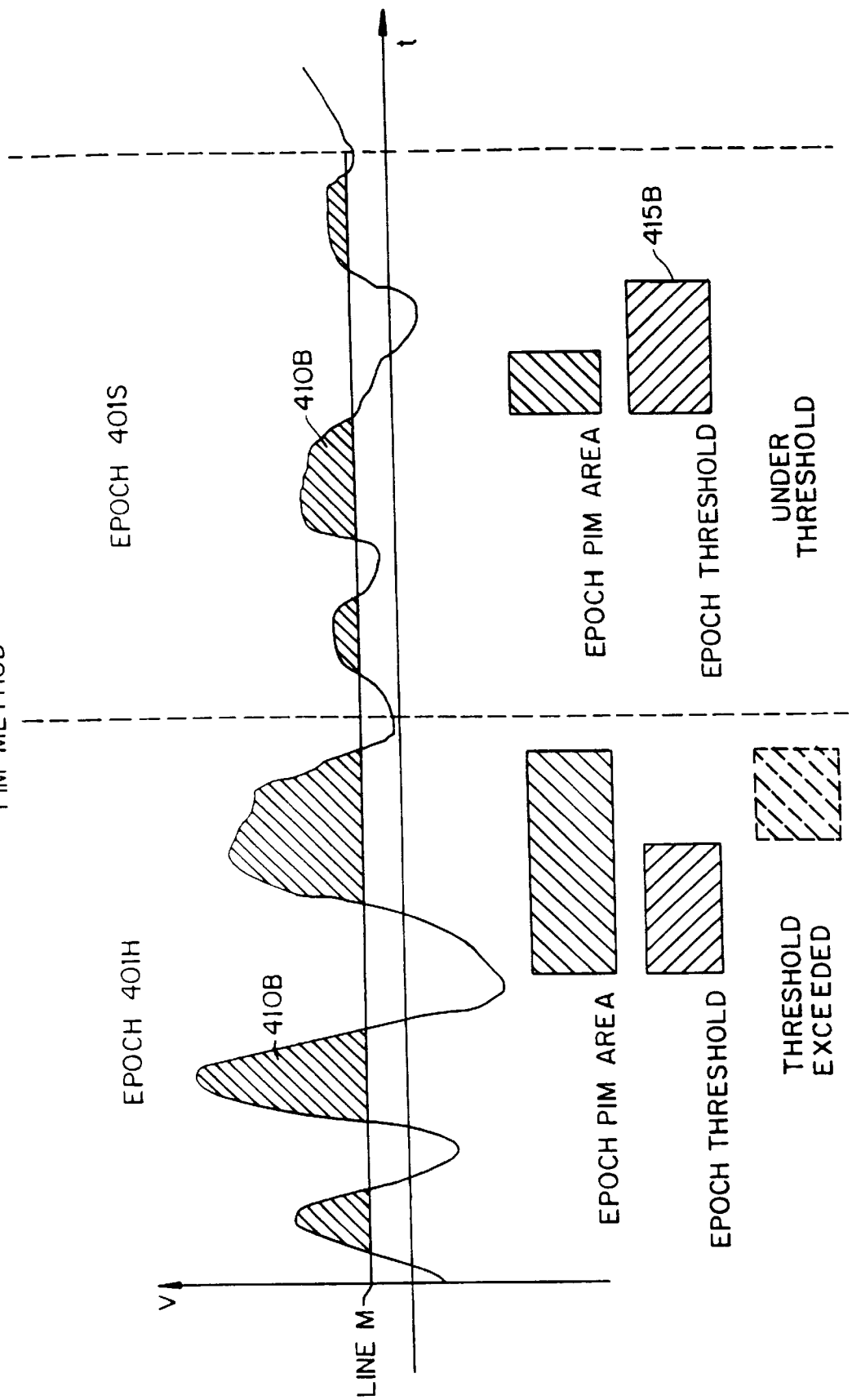

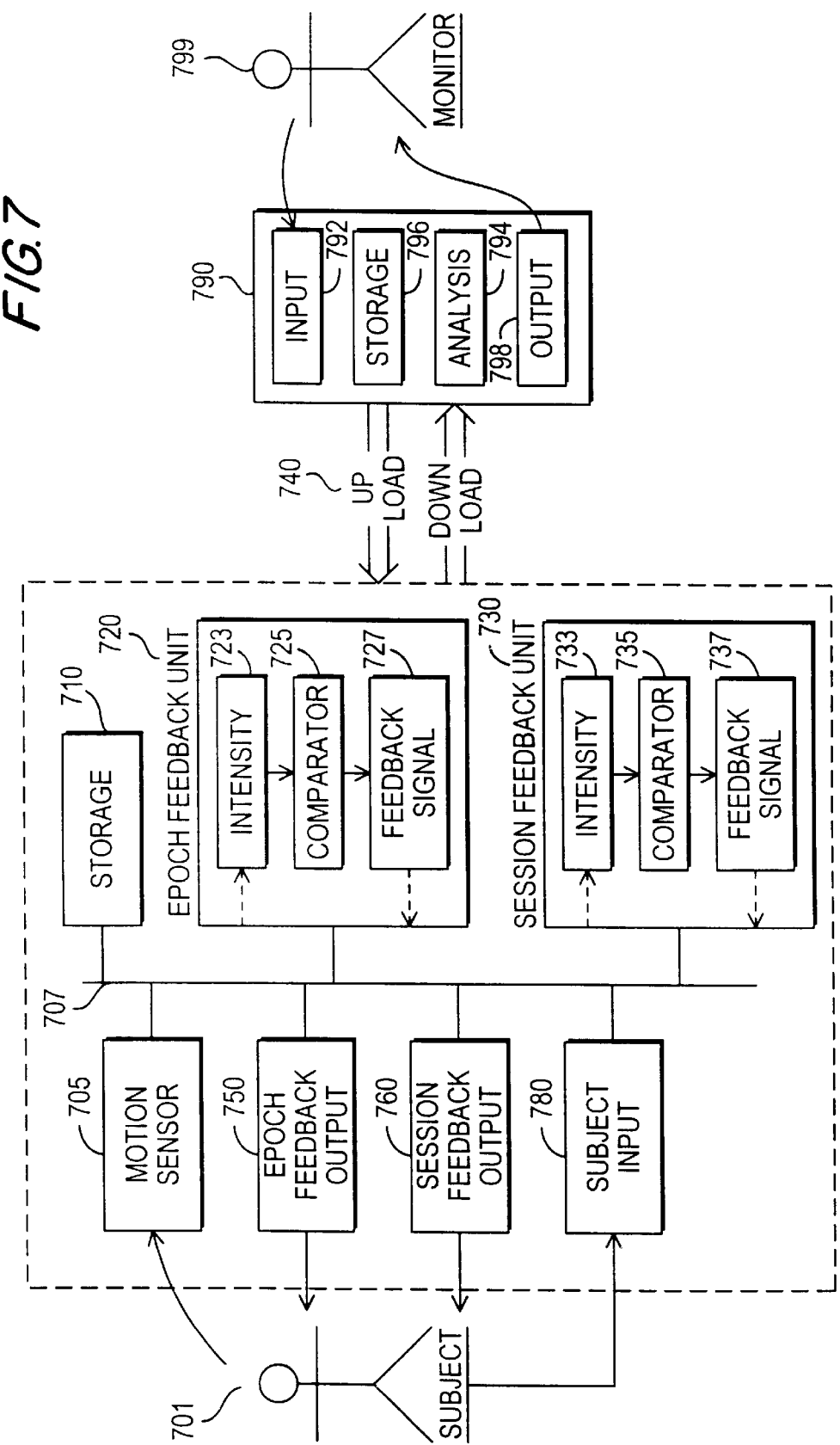

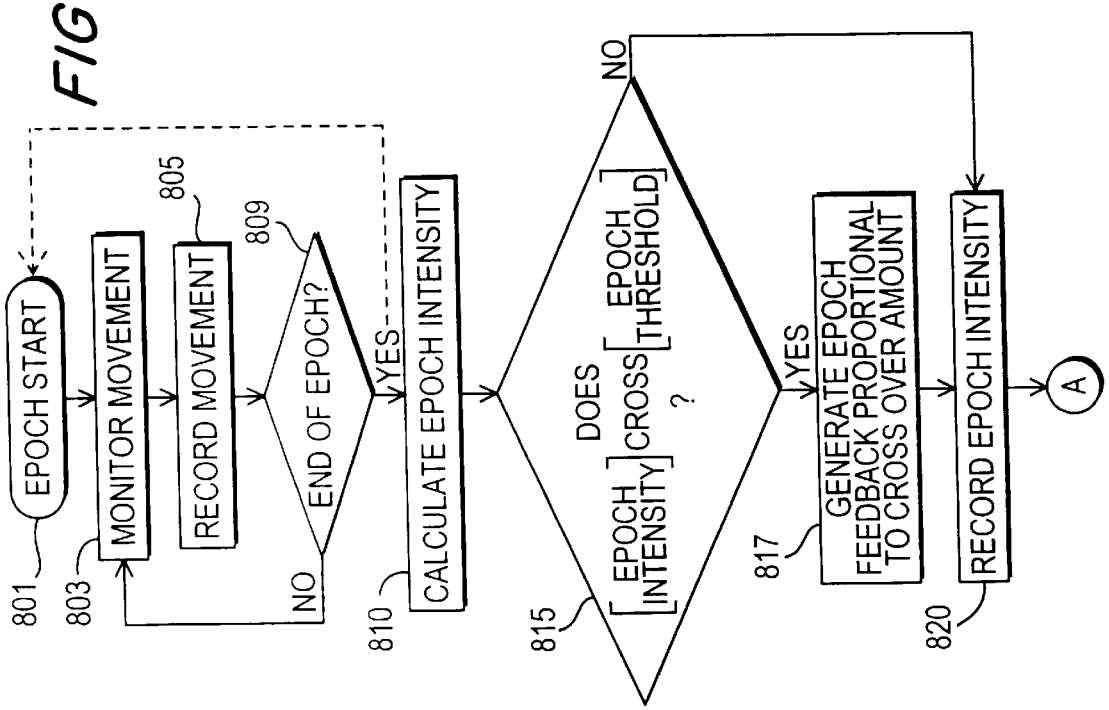
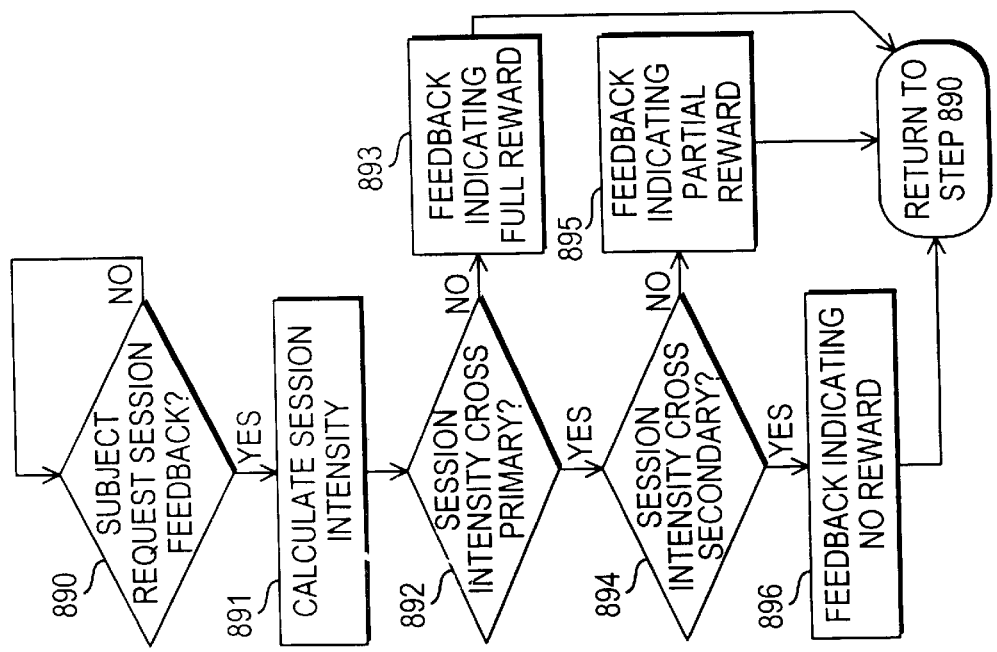
FIG.8

SYSTEM AND METHOD OF MONITORING AND MODIFYING HUMAN ACTIVITY-BASED BEHAVIOR

RELATED APPLICATIONS

This application claims priority from U.S. Provisional Patent Application Serial No. 60/177,778 which was filed on Jan. 24, 2000.

BACKGROUND OF THE INVENTION

1. Field of the Invention

The present invention relates generally to a system and method for monitoring the activity level of one or more individuals and modifying the behavior of those individuals based on feedback from the activity monitoring.

2. Description of the Related Art

According to the National Institutes of Health (NIH), hyperactivity, or Attention Deficit Hyperactivity Disorder (ADHD), is the most commonly diagnosed behavior disorder in children. ADHD affects 3% to 5% of school age children and it is estimated that it accounts for 30% to 50% of all child referrals for mental health services. At present, it is widespread practice in the mental health community to prescribe psychostimulant medication to treat ADHD. However, there is a lack of safety information concerning the long-term effects of psychostimulant usage on children. This lack, in combination with the negative side effects that can occur with psychostimulants and growing parental concerns over the chronic medication of children during their formative years, has created a need for a pharmacologically free technology for reducing hyperactivity.

In the area of ADHD, a pharmacologically free technology has developed that relies upon feedback and operant conditioning in order to modify the behavior of the hyperactive child. An example of such pharmacologically free technology is shown in U.S. Pat. No. 4,112,926 issued to Schulman et al. (hereinafter referred to as "the '926 patent"). In the '926 patent, the hyperactive child wears an activity measuring device which provides feedback to the hyperactive child by means of a set of headphones. Such activity measuring devices are called "actigraphs" in the field of human activity research. The '926 patent activity measuring device is worn around the waist and contains three mercury switches. When there is movement, the mercury is displaced, and the contact in the switch is opened. Each mercury switch is oriented at an 120° angle to the others in order that movement in any direction will be detected. Each time any of the switches are opened, it is registered in a counter, which is periodically reset. If the number of counts registered in the counter reach a specified threshold before the counter is reset, an "excess rate" signal is triggered which causes the headphones to generate an audio signal, thus informing the hyperactive child that he or she has exceeded his or her allotted threshold of movements per time period. Two other counters maintain running totals of the number of excess rate signals and the number of generated movement signals. These running totals may be downloaded and analyzed.

Although the '926 device was demonstrated to be efficacious, it was not commercially successful. The set of headphones was heavy and cumbersome, obstructing both interaction with others and normal movement by the child. Furthermore, the headphones were a conspicuous emblem of the child's hyperactivity, one sure to be noticed by other children. Besides providing no privacy to the child, the obstructive nature of the headphones might skew any experimental results. In addition, the feedback in the '926 device was limited to headphones or possibly a lightbulb. Because of the nature of the circuitry in the '926 device, the headphones or lightbulb would only have one predetermined time period of sound or one predetermined time period of light, respectively, in order to inform the child of his or her own hyperactivity. There was no indication of the intensity of the hyperactivity so that the child may more accurately gauge and modify his or her conduct. Because only the crossing of the movement threshold is recorded, the experimenter also has no way of knowing or analyzing the intensity of the hyperactivity. Further still, the child only receives instantaneous alarms when the number of his or her movements exceeds a threshold but does not have access to the current cumulative totals and, thusly, the child does not know its average activity level over time.

From the perspective of the person using the activity monitor to analyze and/or modify the activity level of the child, the '926 device is lacking in various other ways. For instance, one cannot get information from the activity monitor except by physically interacting with it. This may be done at the end of a session or experiment, but provides no means for one to ascertain the present status of the activity monitor during a session or experiment without being unduly disruptive. This is also problematic for caretakers, such as teachers, who may need to focus on many other details during the day, thus being unable to monitor the child's progress. Because the threshold set in the '926 device could only be changed by manually manipulating the activity monitor, it is difficult for the '926 device to accommodate certain times when an increased or decreased level of activity is expected, such as lecture time or recess for children.

The measurements taken by the '926 device are also lacking. First, as noted above, only the cumulative totals are provided to the experimenter or therapist, allowing no analysis of the child's activity level at different times of day. Second, even if the cumulative running totals were downloaded several times within a session in order to create more than one data point, these running totals would still not provide the ability to analyze the activity level of the child as it changed over the time from the initialization of the activity monitor or from the last download from the activity monitor. Third, as also noted above, the intensity of the hyperactivity is neither monitored nor recorded and, thus, cannot be analyzed.

Therefore, there is a need for a system and method for monitoring and modifying the activity levels of hyperactive children in which the activity monitoring device is neither bulky nor conspicuous. The system and method should be able to monitor the intensity of the movements of the hyperactive child, as well as monitoring the level of physical movement, which is merely the number of movements per unit time. Further, the system and method should record how the intensity of the physical movements changes over time so that a more detailed analysis of the child's activity may be made. The system and method should allow for more elaborate forms of feedback for the hyperactive child, so that the child may understand how he or she is performing over longer time spans. Furthermore, there is a need for a system and method for monitoring and modifying the activity levels of hyperactive children in which data may be downloaded from the activity monitor without interfering with the child's activity.

SUMMARY OF THE INVENTION

It is an object of the present invention to provide a system and method for monitoring and modifying the activity levels of one or more subjects.

It is another object of the present invention to provide a system and method for monitoring and modifying the activity levels of one or more subjects without using monitoring equipment which is bulky or conspicuous.

It is another object of the present invention to provide a system and method for activity monitoring and modification which uses the intensity of physical activity rather than the number of physical movements in order to measure the activity level of one or more subjects.

It is another object of the present invention to provide a system and method for monitoring the behavioral patterns of one or more subjects in which the changes in the activity level of one or more subjects over a time period are recorded, rather than just the final cumulative counts of physical movements over that time period.

It is another object of the present invention to provide a system and method of behavioral modification in which detailed feedback is provided to one or more subjects so that one or more subjects may monitor their own progress over extended periods of time.

It is yet another object of the present invention to provide a system and method of monitoring the behavioral patterns of one or more subjects in which the results of the monitoring may be remotely downloaded from the activity monitor without apparent physical interaction with the activity monitor.

These and other objects are accomplished by the present invention, in which, according to one aspect of the present invention, there is provided a method of modifying an activity level of a subject, said subject being one of a human being and a primate, comprising the steps of: detecting a level of physical movement of a subject; measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated; determining whether an epoch intensity measurement crosses an epoch threshold; and sending, if the epoch intensity measurement crosses the epoch threshold, an epoch feedback signal to one of the subject and a monitor.

According to another aspect of the present invention, a method of modifying an activity level of a subject, said subject being one of a human being and a primate, is provided, comprising the steps of: detecting a level of physical movement of a subject; measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated; determining whether an epoch intensity measurement crosses an epoch threshold; and sending, if the epoch intensity measurement crosses the epoch threshold, an epoch feedback signal to the subject, where said epoch feedback signal is proportional to an amount that the epoch intensity measurement crosses the epoch threshold.

According to another aspect of the present invention, a system for modifying an activity level of a subject, said subject being one of a human being and a primate, is provided, where the system comprises: a motion sensor for detecting a level of physical movement of a subject; means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated; means for determining whether an epoch intensity measurement crosses an epoch threshold; and means for sending, if the epoch intensity measurement crosses the epoch threshold, an epoch feedback signal to the subject, where said epoch feedback signal is proportional to an amount that the epoch intensity measurement crosses the epoch threshold.

According to another aspect of the present invention, a system for modifying an activity level of a subject, said subject being one of a human being and a primate is provided, comprising: a motion sensor for detecting a level of physical movement of a subject; an epoch feedback unit and a session feedback unit. The epoch feedback unit comprises: means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated; means for determining whether an epoch intensity measurement crosses an epoch threshold; and epoch feedback signal means for generating, if the epoch intensity measurement crosses the epoch threshold, an epoch feedback signal, where said epoch feedback signal is proportional to an amount that the epoch intensity measurement crosses the epoch threshold. The session feedback unit comprises: means for recording the epoch intensity measurement at the end of each epoch; means for calculating a session intensity measurement from an average of recorded epoch intensity measurements; means for determining whether the session intensity measurement crosses a session threshold; and session feedback signal means for generating a session feedback signal, where said epoch feedback signal is proportional to an amount that the session intensity a measurement crosses the session threshold.

According to another aspect of the present invention, there is provided a method of modifying an activity level of a subject, said subject being one of a human being and a primate, comprising the steps of: detecting a level of physical movement of a subject; searching for a match between the detected level of physical movement and a predetermined pattern of physical movement; and sending, if there is a match between the detected level of physical movement and the predetermined pattern of physical movement, a pattern recognition feedback signal to the subject.

Other objects, aspects, and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended, to conceptually illustrate the structures and procedures described herein.

BRIEF DESCRIPTION OF THE DRAWINGS

In the drawings:

FIGS. 4A and 4B show graphs of the same line of activity level over time, where activity intensity is measured by the Zero Crossing (ZC) method and the Proportional Integrated Measure (PIM) method, respectively;

FIG. 7 is a conceptual model of various embodiments of the present invention.

DETAILED DESCRIPTION OF THE PRESENTLY PREFERRED EMBODIMENTS

The present invention may be used for both monitoring and modifying activity-based behavior in certain animals, including humans and primates. Therefore, although the presently preferred embodiments below refer to children with ADHD (FIG. 1) and an elderly patient with Alzheimer's Disease (FIG. 2), it should be understood that the present invention may be applied to any condition which expresses itself in behavioral activity with discernible characteristics.

Figure 1:
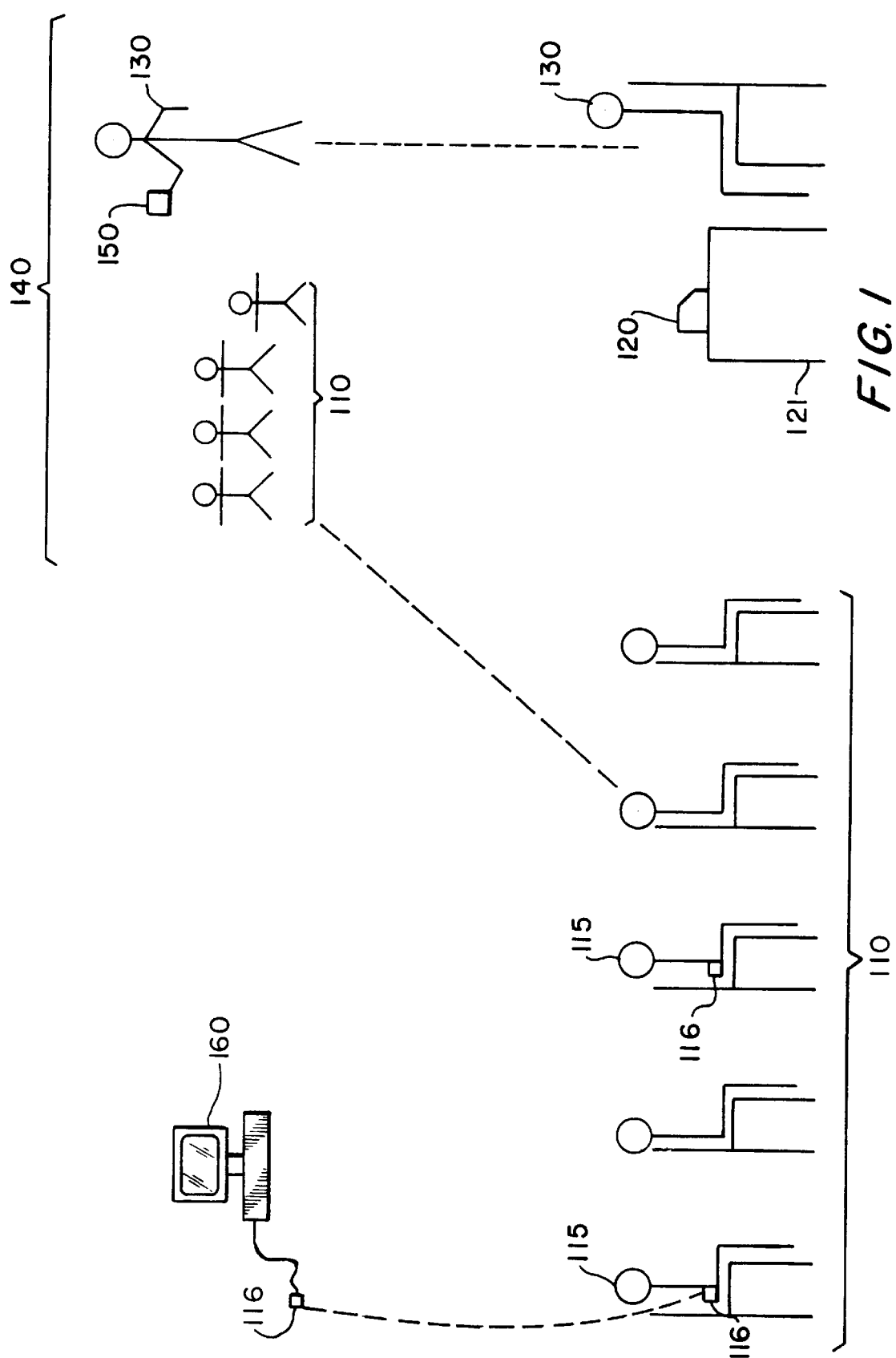
FIG. 1 is a block diagram of a hyperactivity behavior modification system according to a preferred embodiment of the present invention.

A preferred embodiment of the system of the present invention is shown in FIG. 1. FIG. 1 shows a classroom with many students 110, some of whom have ADHD 115 and whose behavior is being modified. Attached to the waist of each ADHD student 115 is an activity monitor 116 which is about the size of a conventional pager. Each activity monitor 116 provides vibrotactile feedback to the ADHD student 115 wearing it. Such feedback is presently preferred because it is unnoticeable to other students in close proximity to the ADHD child. In the preferred embodiment, each activity monitor 116 comprises an motion sensor, a vibro-motor and controls, a radio transceiver, feedback logic, firmware, and a non-volatile memory. In addition, three LEDs are provided at the top of the pager-like activity monitor 116.

It has been found through experimentation that, while activity monitor 116 is giving vibrotactile feedback, it is preferable that the motion sensor continue monitoring the activity of the ADHD child. Unfortunately, when such monitoring is performed, the vibrotactile feedback alters the readings taken by the motion sensor. In the preferred embodiment, the motion sensor comprises a pair of piezoelectric bimorph beams which are capable of suppressing either rotational or translational motion while simultaneously monitoring the remaining unsuppressed motion. Such a specialized motion sensor is described in a patent application entitled "Motion Sensor and Method of Making Same" to be filed by inventor Robert Conlan and assigned to Precision Control Design, Inc. The noise cancellation technique described therein will improve the signal-to-noise sufficiently so that analog or digital filters may be used to isolate the desired signal (the ADHD child's movements) from the noise (the vibrations of the activity sensor).

In other embodiments, activity monitor 116 may take the form of a watch-like device worn on the wrist, or may comprise a number of inconspicuous sensor patches worn at different spots on the ADHD child's body. In the future, technologies may be available in which the ADHD child is monitored remotely by a video camera without any attachments to the ADHD child's body. In such an embodiment, the video camera would be controlled by an image recognition program that was adapted to recognize individual children and the level of activity they are exhibiting.

The feedback logic along with the operating system programmed into the non-volatile memory control the feedback provided to the ADHD child. In the preferred embodiment, two types of feedback are given to the ADHD child. Instantaneous feedback, which concerns the child's present level of activity, is in the form of tactile vibrations generated by the activity monitor and session feedback, which concerns the child's overall level of activity from the beginning of the session to the present time, is in the form of differently colored LEDs on the activity monitor. The instantaneous feedback provides the ADHD child with continuous self-monitoring, while the session feedback provides the ADHD child long-term goals to be achieved. Each ADHD child is given, or not given, rewards at the end of the session based on the session feedback. Session feedback is based on one or more session thresholds and, when different levels of session thresholds are employed, different levels of rewards may be given, as will be described more fully below.

In the preferred embodiment, each type of threshold (instantaneous and session) has two levels, a primary threshold and a secondary threshold. The two instantaneous feedback thresholds are both used to provide vibrotactile feedback in the form of pulses of varying lengths. This vibrotactile feedback is proportional to the intensity of the activity of the ADHD child. The purpose of the vibrotactile feedback is to teach the ADHD child when he or she is exhibiting hyperactivity. The fact that, in the preferred embodiment, the vibrotactile feedback is proportional with the intensity of movement of the child provides another level of self-awareness for the child. This proportionality will be discussed further below.

Figure 3A:
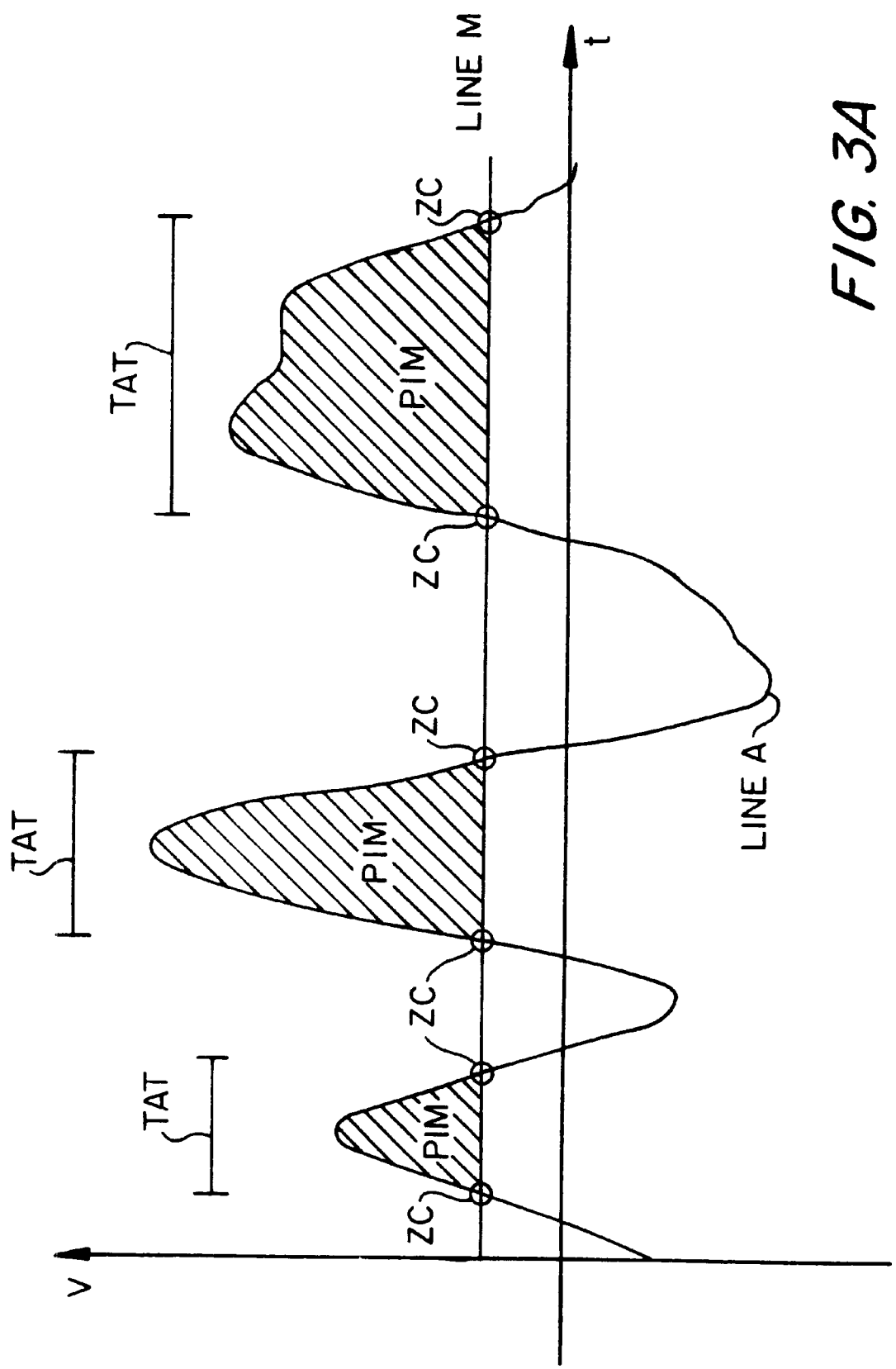
FIGS. 3A and 3B are graphs of the activity level of an ADHD child over time, in unrectified and rectified form, respectively, in which three different ways of measuring activity intensity are shown.
Figure 3B:
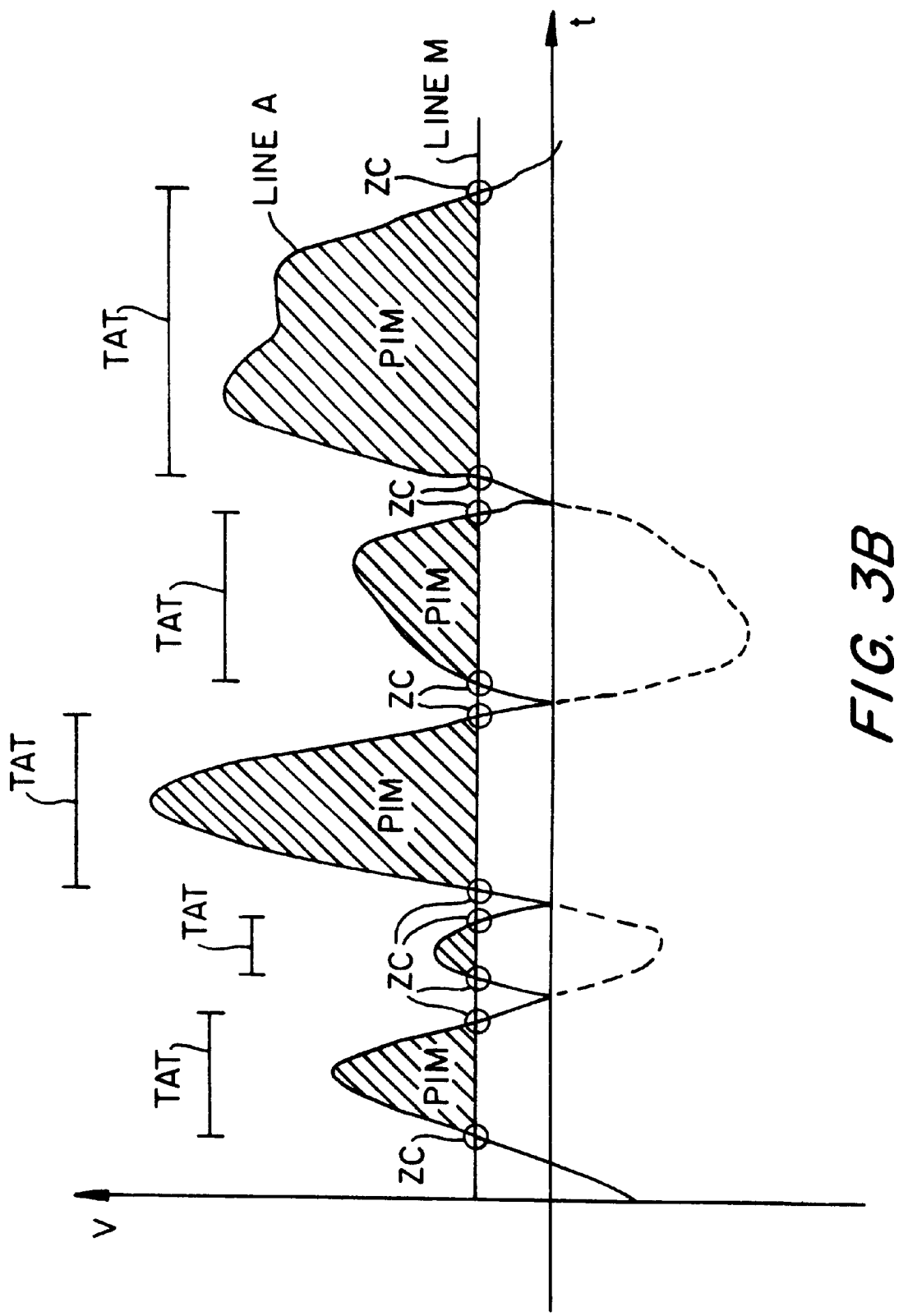

The intensity of activity may be measured in many ways, three of which will be described with reference to FIGS. 3A and 3B. FIG. 3A shows the varying activity level of a child over time, as represented by line A, and three different ways to measure the intensity of the activity level of that child: the number of zero crossings (ZCs) of line A, the amount of time that line A spends above a movement threshold line M (TAT), and the amplitude of movement of line A above the movement threshold line M integrated over time, or Proportional Integrated Measure (PIM). The thresholds of each of these measurement methods is determined every predetermined period of time, or epoch, in relation to a set physical movement threshold, as represented by line M. The number of ZCs is the number of times line A crosses movement threshold line M per epoch. In this context, an instantaneous feedback threshold would be a set number of ZCs in an epoch. The amount of time TAT is measured from the instant the child's movement exceeds the movement threshold line M to the instant that the child's movement is back below the movement threshold line M. In this context, an instantaneous feedback threshold would be a set amount of accumulated TAT time per epoch. The PIM is the area between the line A of present movement of the child and movement threshold line M. In this context, the instantaneous feedback threshold would be a set amount of accumulated PIM area per epoch. It should be noted that physical movement threshold line M may be set anywhere, including where the level of activity is zero (e.g., the x-axis). Physical movement threshold line M, and the epoch threshold or thresholds, may be set by software or hardware in the activity monitor 116, or by remote control. FIG. 3B has the same input as FIG. 3B, but it has been rectified, so that values below the zero line (or x-axis) are reflected back up above the zero line.

The ZC method of measurement is most nearly analogous to the measurement method used in the prior art '926 device. However, when using the ZC method in an embodiment of the present invention, fine gradations of movement can be analyzed and the movement threshold may be set at different levels. In the '926 device, the movement threshold is coarsely defined as whenever a contact in one of the three mercury switches is broken and the instantaneous threshold is set as one count level of these coarse movements in a counter. Furthermore, when using the ZC method in an embodiment of the present invention, the movement threshold line M may changed by a teacher or experimenter to different levels at different times (this will be discussed more fully below). There is no means of doing this in the middle of a session in the '926 device. Because of these differences, an embodiment of the present invention which uses the ZC method can more effectively measure the intensity of the monitored child's movements, rather than merely the number of the monitored child's movements, as the '926 device.

Even though the ZC method as used by embodiments of the present invention is superior to the coarse counting method used by the '926 device, the presently preferred embodiment of the present invention uses the PIM method, which is even more superior to the '926 device method. During experimentation regarding the present invention, it was discovered that the ZC method did not adequately discriminate between hyperactive behavior and normally active behavior. This can be seen in reference to FIGS. 4A and 4B. Both FIGS. 4A and 4B have the same input data, namely, line 401 indicating the level of movement of the ADHD child. In the presently preferred embodiment, the level of movement corresponds to the amount of voltage generated by a transducer in the piezoelectric bimorph sensor mentioned above. Line 401 is taken over two epochs: epoch 401S is an epoch during which the child is sitting quietly working and epoch 401H is an epoch during which the child is exhibiting out-of-seat hyperactive behavior.

Both FIGS. 4A and 4B have an identical movement threshold, as indicated by line M. On the one hand, FIG. 4A uses the ZC method to determine when the instantaneous feedback threshold has been exceeded. This is done by keeping a count of the accumulated number of zero crossings (indicated at points labeled by reference numeral 410A) during an epoch. This recorded number is compared with the instantaneous feedback threshold, which is 5 zero crossings (ZCs), as indicated by reference numeral 415A. Because there are 6 ZCs in both epoch 401S and epoch 401H, instantaneous feedback is generated in both epochs, even though the amplitude of the child's movements in epoch 401S is relatively small. During experiments, this resulted in children complaining that the activity monitor "buzzed too much", meaning that vibrotactile feedback was generated in what seemed to be fairly calm periods, e.g., when sitting, as in epoch 401S.

On the other hand, FIG. 4B uses the PIM method to determine when the instantaneous feedback threshold has been exceeded. This is done by keeping track of the amount of area between movement line A of the child and movement threshold line M, as shown by the areas with diagonal lines with reference numeral 410B. The amount of area 410B accumulated in an individual epoch is compared against the instantaneous feedback threshold 415B, which is a reference area amount. Because the amount of area accumulated in epoch 401S is less than threshold 415B, no feedback is generated in epoch 401S. Because the amount of area accumulated in epoch 401H is greater than threshold 415B, fibrotactile feedback is generated in epoch 401H. This provides much more accurate feedback to the ADHD child being monitored.

Thus, the presently preferred embodiment uses the PIM method to measure the intensity of the monitored child's activity. As discussed above, either when monitoring the intensity level over the present epoch in order to generate instantaneous feedback or monitoring the average intensity level as measured from the beginning of the session in order to generate session feedback, two levels of thresholds are used in the presently preferred embodiment: a primary threshold and a secondary threshold. In the preferred embodiment, the ADHD child is monitored for a period of time to determine a baseline mean of activity for that child. Then the threshold levels are set according to the determined baseline mean of activity. For the instantaneous thresholds, the primary level is set at the mean baseline activity level and the secondary level is set at the mean plus two standard deviations. For the session thresholds, the primary level is set at approximately 20% below the baseline mean and the secondary level is set at one standard deviation below the baseline mean. The session thresholds are below the instantaneous thresholds because they represent the "goal" values being sought for the child being monitored. 20% below mean was chosen as the primary goal because previous experimentation has indicated that this is a realistic aim for most ADHD children. A standard deviation below the baseline was chosen as a secondary goal in order to insure that some significant reduction in activity, even if it does not reach the primary goal, is awarded with some recognition.

In the preferred embodiment, the following feedback behavior is generated when thresholds are exceeded. No vibrotactile feedback is generated when the intensity level in an epoch is below the primary instantaneous threshold level. As mentioned above, when the intensity level in an epoch exceeds the primary instantaneous threshold level, vibrotactile feedback that is proportionate to the amount in excess of the primary threshold is generated. In the presently preferred embodiment, this vibrotactile feedback has five increasing steps of proportionate response, ranging from 0.5 seconds to 5 seconds. When the intensity level in an epoch is greater than the secondary instantaneous threshold level, the 5 second pulse is generated, warning the child that he or she has greatly exceeded the appropriate limit. When the intensity level in an epoch is just above the primary instantaneous threshold, the 0.5 second pulse is generated, indicating to the child that he or she has just reached the initial boundary of activity level excess. There are gradually increasing steps in between these two values, from the initial value of 0.5 seconds to the final value of 5 seconds, each step being proportionate to the intensity of the excess activity. This is only one means of determining proportionate feedback, and many other means are possible. For instance, rather than step-wise increases, the increases could be continuously proportionate to the intensity level measured in an epoch.

In the preferred embodiment, the session thresholds provide another means for the ADHD child to evaluate his or her own current performance, but in relation to a long-term (session) goal, rather than a short-term (epoch) goal. In this manner, the ADHD child may attempt to "make up" for periods of excessive activity intensity by attempting to minimize activity intensity for a period of time. In order to increase this incentive, rewards are offered to the monitored ADHD child depending on the cumulative average activity intensity level at the end of the session in the preferred embodiment. The length of a session may be any period of time longer than an epoch, such as a class period, a morning, or an entire school day. The ADHD child can ascertain his or her current cumulative average intensity level in comparison to the primary and secondary session thresholds by pressing a button on the activity monitor. When this button is engaged, one of three differently colored (green, amber, and red) LEDs lights up. In the presently preferred embodiment, when the present cumulative average intensity level is below the primary session threshold, the green LED lights up. When the present cumulative average intensity level is above the secondary threshold, the red LED lights up. For any cumulative average intensity level between the primary and secondary session thresholds, the amber LED lights up.

In the preferred embodiment, two different types of rewards are given to some of the children at the end of the session, based on which color LED lights up at the end of the session, i.e., the final average intensity level. The most desirable items are given to those whose green LED lights up at the end of the session, while other desirable items are given to those whose amber LED lights up at the end of the session. No items are given to those whose red LED lights up at the end of the session. In this manner, the ADHD children who succeed in significantly reducing their activity intensity from their normal baseline level are rewarded depending on the amount of activity reduction achieved.

Although these four thresholds (two epoch and two session) are used in the preferred embodiment, additional thresholds, with their own feedback, may be used. For example, there might be an additional rule for the ADHD child that if the secondary epoch threshold is exceeded three or more times in a certain time period (such as two minutes), another type of feedback is generated. In such an embodiment, this rule could be applied as "three strikes, you are out", meaning that if this three times threshold is exceeded, the red LED turns on permanently (i.e., the rest of the session) indicating that the child's behavior has reached a point where no presents will be given.

Figure 8:
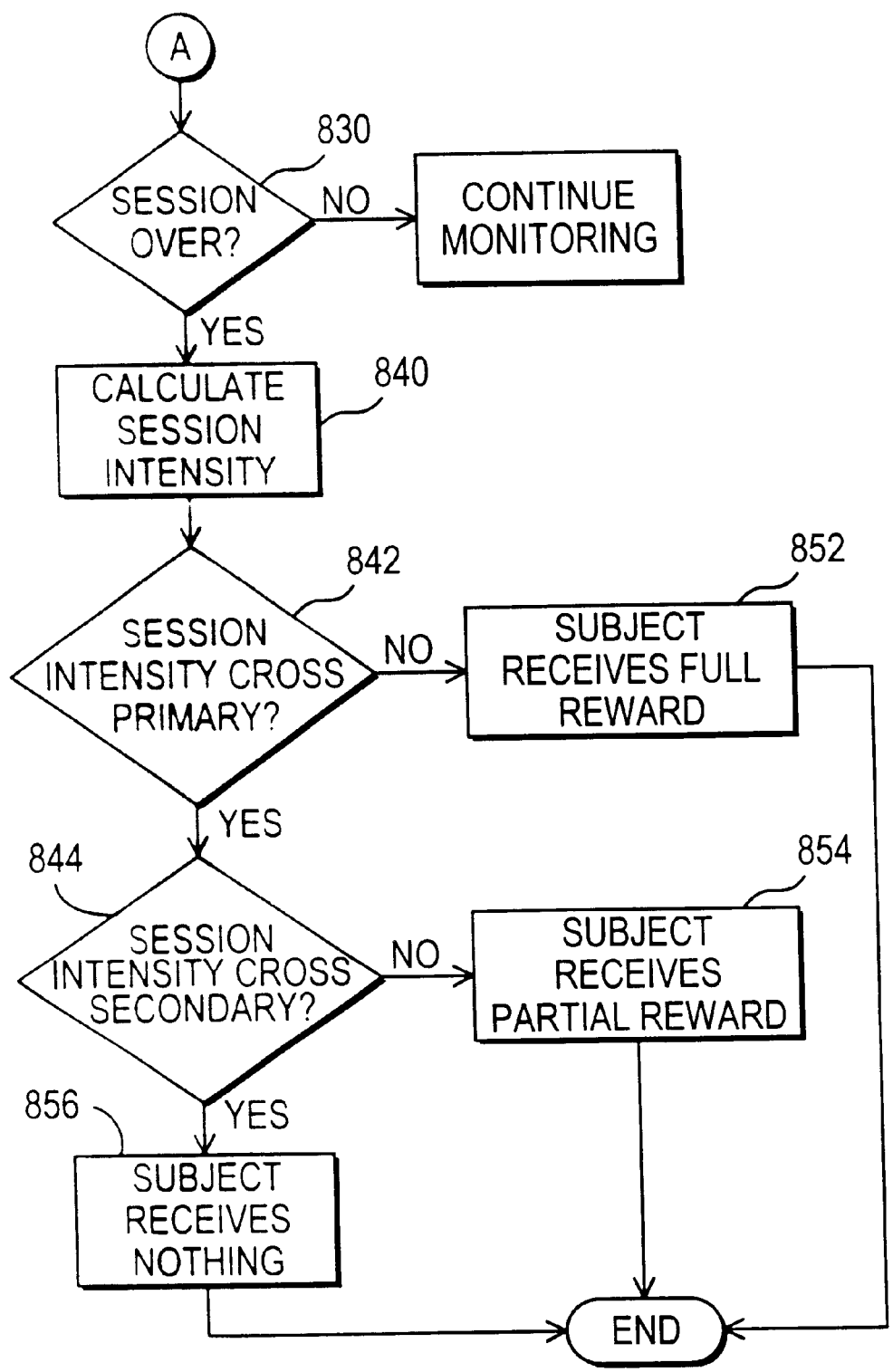
FIG. 8 is a flowchart of a behavioral modification feedback method according to a preferred embodiment of the present invention.

FIG. 8 is a flowchart of the steps that may be performed by activity monitor 116 when implementing the above preferred embodiment of the present invention. These steps may be performed in a different sequence, and some steps may be added or subtracted, according to the needs of different embodiments. Furthermore, although the steps are shown in sequential order, many of them may be performed simultaneously. In FIG. 8, an epoch starts at step 801 and movement is continually monitored (step 803) and recorded (step 805). Steps 803 and 805 form a continuous loop that ends when it is determined that the epoch has reached an end, at step 809. Then, the intensity of the epoch that just ended is calculated at step 810. The dotted line leading from step 810 back to step 801 is to indicate that, although other procedures are being performed, the next epoch starts immediately at the end of the last epoch.

In step 815, it is determined whether the epoch intensity calculated in step 810 crosses the epoch intensity threshold. The term "cross" is used here because the threshold may be a minimum or a maximum, so that either going above (when it's a maximum) or going below (when it's a minimum) the threshold is signified by the phrase "crossing the threshold".

In embodiments involving hyperactivity, the epoch threshold is a maximum threshold; whereas, in embodiments involving hypoactivity, the epoch threshold is a minimum threshold. If the epoch intensity crosses the epoch intensity threshold, epoch feedback is generated in step 817. In the preferred embodiment, this feedback is in the form of tactile vibrations whose duration is proportional to the amount the epoch intensity crossed the epoch intensity threshold. The secondary epoch threshold acts as an upper limit to the proportionality (i.e., the duration of the vibrations will be up to five seconds long, but no more), so there is no need for an additional step. However, in other embodiments which have either multiple thresholds or multiple threshold levels for each epoch, additional steps would be added.

After the epoch feedback is generated in step 817, or if the epoch intensity did not cross the epoch threshold in step 815, the calculated epoch intensity is stored at step 820. In the preferred embodiment, during step 817, the level of the generated epoch feedback is recorded. It should be noted that this is not necessary, because the level of generated feedback can be determined from the epoch intensity, which is recorded in step 820. After step 820, it is determined, in step 830, whether it is the end of the session. This could be done by either predefining the session as lasting a certain time period and then counting down, or determining whether a command to end the session has been received.

If it is the end of the session in step 830, the session intensity is calculated in step 840. In the preferred embodiment, this calculation involves averaging the epoch intensities stored in step 820; however, it is possible to use other definitions of session intensity. At this point, it is determined whether the calculated session intensity crosses a primary threshold at step 842. If it does not, a full reward is given to the subject in step 852. If the session intensity does cross the primary threshold, it is determined whether the session intensity crosses the secondary threshold in step 844. If it does not, a partial reward is given to the subject in step 854. If the session intensity does cross the secondary threshold in step 844, the subject receives nothing in step 856 and the procedure ends. Similarly to the epoch thresholds, other embodiments may have either multiple thresholds or multiple threshold levels for each session, thus requiring additional steps to be added to the method.

An additional loop consisting of steps 890 to 895 and unconnected to steps 801–856 is shown in FIG. 8. This loop represents the ability, in the preferred embodiment, of the ADHD child to ask for his or her current session intensity level, and, as such, is separate from the other sequential steps. In step 890, it is determined whether the subject has requested feedback concerning his or her current session intensity level. When the subject does make the request, the current session intensity is calculated in step 891. After calculating the session intensity in step 891, the process continues with step 892, where it is determined whether the calculated session intensity crosses a primary threshold. If it does not, a feedback signal indicating that the subject is on track for receiving a full reward is generated in step 893. If the session intensity does cross the primary threshold, it is determined whether the session intensity crosses the secondary threshold in step 894. If it does not, a feedback signal indicating that the subject is on track for receiving a partial reward is generated in step 895. If the session intensity does cross the secondary threshold in step 894, a feedback signal indicating that the subject is on track for receiving no reward is generated in step 896. After the appropriate feedback is generated, the process returns to step 890.

Although, in the preferred embodiment, LEDs are used to provide feedback concerning the average intensity over the entire session, other means are contemplated for providing session feedback in other embodiments. For example, an LCD which continually displays the average cumulative intensity in a numeric or iconic format might be used. In an embodiment employing an LCD, the LCD could also display information concerning instantaneous feedback, such as the number of times instantaneous feedback was generated and the various levels of the generated instantaneous feedback. Likewise, other means besides tactile vibrations and visual displays may be used to provide instantaneous (epoch) feedback to the monitored child. For instance, auditory feedback might be used. In the preferred embodiments, the length of time of the vibrotactile pulse provides epoch feedback proportional to the amount of activity intensity over the epoch threshold. In other embodiments, any variation in feedback which is easily differentiated by the subject could be used. For example, the length of time of a vibrotactile pulse may remain constant, and the amplitude or the pulsation pattern may vary so as to provide proportional feedback to the subject.

Furthermore, in addition to other forms of feedback, other embodiments of the present invention may use different thresholds to generate feedback. For example, in another embodiment, there might not be separate session and instantaneous threshold levels, but merely instantaneous threshold levels which are compared to both the epoch intensity and the average session intensity. In other embodiments, other types of thresholds might be employed, such as a threshold for average intensity taken over a sliding window in time or a threshold for abrupt movements as represented by a steep line in a graph like the one shown in FIGS. 4A and 4B. Different thresholds may require that different sorts of measurements be taken and recorded. This, of course, implies that different types of movement phenomena may be measured and, thusly, different definitions of intensity may be employed. In addition, more or less levels than just two (a primary and a secondary) may be used for each threshold.

One example of a different type of threshold would be a "scratching" threshold. If it is desired to stop a particular behavior (e.g., scratching), a specific activity signature for that behavior would be created. This specific activity signature would correspond to a specific series of activity level changes over time. If the system recognizes that the subject's present behavior is within a certain degree of similarity with the specific activity signature, the "scratching" threshold will be considered crossed, and appropriate feedback would be generated. Furthermore, as stated above, if different types of thresholds are employed, they might require that different sorts of measurements be taken and recorded. For example, in an embodiment where patch sensors are placed at different points on the subject's body, a simultaneous combination of input, which corresponds to a prohibited behavior, might serve to trigger a threshold warning.

Now that the activity monitor 116 and some exemplary ways by which it may measure activity intensity have been described, we return to FIG. 1 in order to describe the remaining components in the hyperactivity behavior modification system according to a preferred embodiment of the present invention. Desktop Transceiver (DTR) 120 is the primary autonomous method of communication with the different activity monitors 116. Preferably, as shown in FIG. 1, DTR 120 resides at the teacher's desk 121 in a classroom setting and is under the control of an adult supervisor, most likely a teacher 130, who is monitoring the system. DTR 120 features a control panel and a display for user input/output. DTR 120 also has an antenna, either integrated into the unit itself or attached by a wire, and the antenna maintains a two way wireless communication link with the various activity monitors 116. This multiple access wireless communication link may be implemented in a variety of ways. For example, a short range radio frequency (RF) wireless protocol such as Bluetooth may be used, in which all of the network elements share the same channel using time division multiplexing. The DTR would act as the master. As another example, a longer range RF protocol may be used, in which each activity monitor has its own broadcast frequency for a communication link and the monitored child may roam over an entire campus (more than 300 feet) while still maintaining a communication link.

Teacher 130 may use DTR 120 to send specific commands to individual activity monitors 116 or to send a broadcast command to all or some activity monitors 116 in the group. As an example of an individual command, teacher 130 may turn off the activity monitor 116 of a particular student, when that student is engaged in active, but appropriate, behavior. If teacher 130 is knowledgeable enough, teacher 130 may use DTR 120 to lower the thresholds of an ADHD child whom the teacher 130 believes is ready to attempt the next level of self-control. As an example of a broadcast command, teacher 130 may change the threshold settings either up or down during recess or quiet time for the entire group. This does not necessarily mean that the thresholds of all the children are changed to the same setting, for the broadcast command may be a relative one. In other words, the broadcast command may merely indicate that each threshold should be increased (or decreased) by 15%. In that manner, each monitored child may have individualized threshold settings yet the DTR 120 may still transmit group commands. Other examples of broadcast commands include starting or stopping a session, and resetting the system.

While DTR 120 may transmit commands to one or more activity monitors 116, it can also receive different types of information from one or more activity monitors 116. In some embodiments, each activity monitor 116 may continuously transmit its current telemetry so that the DTR 120 may contemporaneously record the monitored child's activity level during the entire session. In such embodiments, the activity monitors 116 would not require much on-board memory but would require a robust communication link and battery system. In addition, such an embodiment would allow the teacher to pull up any monitored child's current and past activity level history and display it for analysis at any time. In other embodiments, each activity monitor 116 may store its own activity level readings, instantaneous feedback counts and levels, etc., for later download. In these embodiments, particular information may be chosen for simultaneous transmission to DTR 120. For instance, each time the child receives instantaneous feedback, the DTR 120 might be informed, so that the DTR 120 also tracks the child's behavior. Or the activity monitors 116 may be fairly passive, and the DTR 120 (either automatically or by teacher 130's request) may intermittently request transmission of certain counts from individual activity monitors 116. Many variations are possible.

The exact manner of implementing DTR 120 is flexible. However, different features would be preferred in different embodiments. For instance, in an embodiment where the DTR might be continuously operating, e.g. downloading data, line power would be preferred over battery power. In most embodiments, a push button keypad would be used for user input, but, in other embodiments, a touchscreen could be used for both entering input and displaying output. In one embodiment, a laptop computer with an attached antenna device is used as DTR 120. In another embodiment, a desktop computer, perhaps one already present on teacher 130's desk 121, is used as DTR 120. In such an embodiment, the implementation of DTR 120 may take the form of merely downloading software into a wireless enabled classroom computer. In other embodiments, DTR 120 has a network connection that allows health professionals to collect data for analysis. This network connection may take the form of a hookup to a hospital's wide area network (WAN) for centralized tracking and patient management or to a school's local area network (LAN) for record-keeping and analysis by the school nurse. In such embodiments, health professionals may provide diagnoses and analyses to ADHD children located in remote areas.

In FIG. 1, teacher 130 is also shown in a location 140 where DTR 120 is not easily accessible. For those occasions, teacher 130 uses Hand-Held Remote (HHR) 150, which is similar in size to a TV remote control. In most embodiments, HHR 150 is not intended to replace DTR 120 and has much less functionality than DTR 120. For example, HHR 150 might have simple button commands, such as "Increase Thresholds", "Decrease Thresholds", "On", and "Off". HHR 150 would be used in situations where there is only one activity monitor 116 in range of its antenna, but it would be possible in some embodiments to identify and therefore control more than one activity monitor 116 in range of HHR 150. In most embodiments, HHR 150 would not be used to download information from the activity monitors 116. However, in some embodiments, an indicator, such as an LED, might be used to indicate that instantaneous feedback is being given by an activity monitor 116 within range of, or identified individually by, HHR 150.

In some embodiments, recorded or transmitted data is stored in a separate personal computer (PC) 160. In such an embodiment, recorded data may be downloaded by a serial connection from individual activity monitors 116 to PC 160 or may receive transmitted data via a communication link with DTR or directly from activity monitors 116. The PC 160 is used for analysis and diagnosis of the downloaded data. As discussed above, in some embodiments, DTR 120 may make PC 160 superfluous. Furthermore, in some contemplated embodiments, future personal digital assistant (PDA) technology may allow the implementation of the functions of HHR 150, DTR 120, and PC 160 in one single portable PDA.

The use of computing devices, whether a PDA, PC, or even a microcontroller in the activity monitor, in different embodiments of the present invention presents the option of using self-modifying operating systems, or Artificial Intelligence (AI). In embodiments employing AI, the system itself may modify operating parameters, such as thresholds, based on what it has "learned" from the history of activity of the particular subject. If robust enough, such systems would "learn" the periods of time during the day and during the week in which recess and quiet time occur, and adjust its parameters accordingly.

Figure 2:
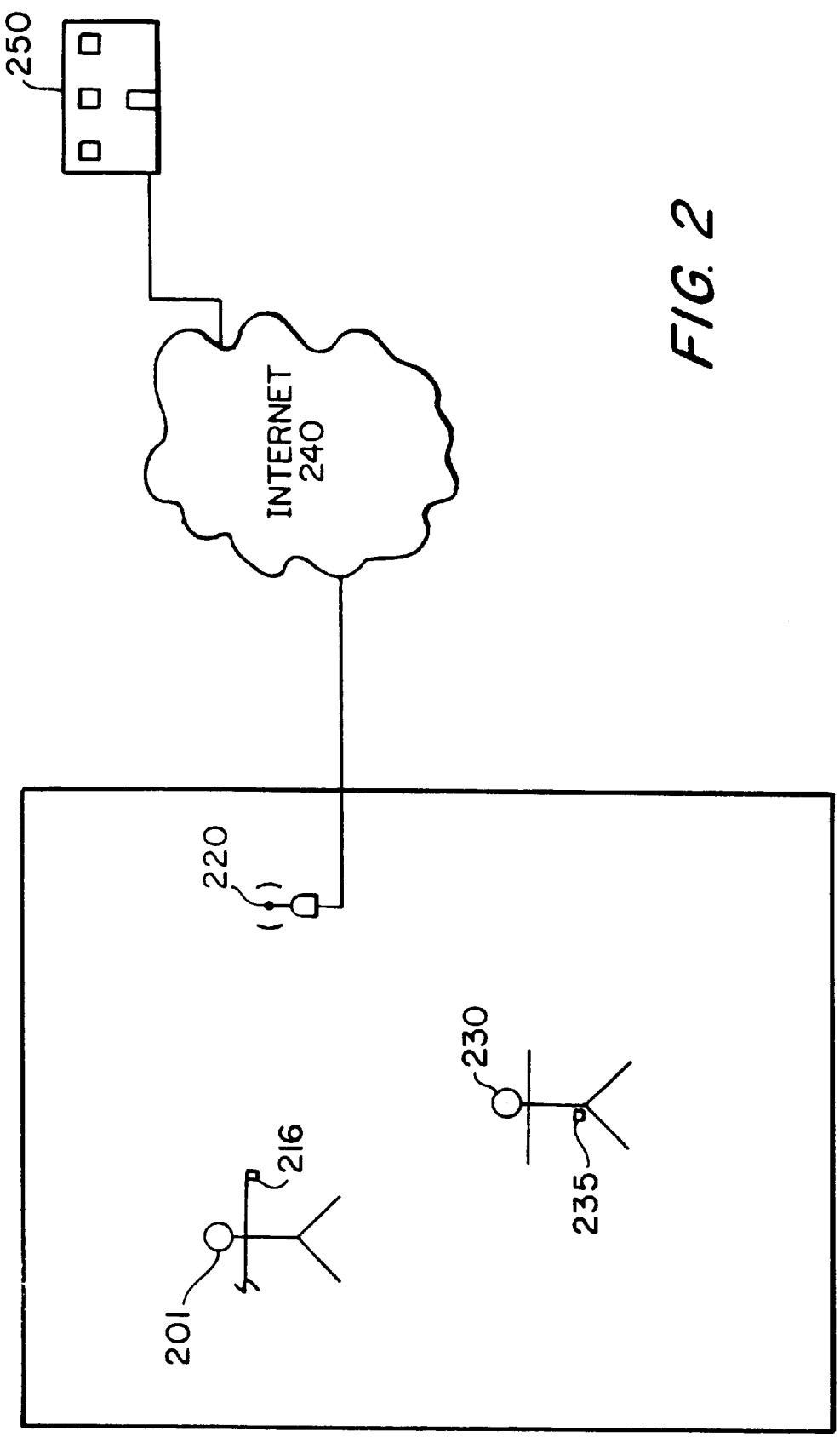
FIG. 2 is a block diagram of a behavior monitoring system according to another preferred embodiment of the present invention.

Although the different components have been described above in reference to a preferred classroom embodiment where hyperactivity is being treated, other embodiments of the present invention may treat other activity disorders or problematic behavior. For example, an embodiment of the present invention may be implemented for use by adults with ADHD in order to improve their work or study capabilities. As another example, the preferred embodiment of FIG. 2 shows an elderly patient 201 who is subject to sundowning and night wandering. "Sundowning" refers to a phenomena occurring in the late stages of Alzheimer's, where the patient becomes highly agitated, active, confused, combatant, anxious, and/or restless in the late afternoon. "Night wandering" refers to a phenomena where the patient confuses night and day, and the patient may wander unsupervised at inappropriate times (i.e., at night).

Elderly patient 201, who has Alzheimer's Disease and is subject to sundowning and night wandering, is living at a rest home and has an activity monitor 216 attached to his wrist. Activity monitor 216 has a wireless communication link with base station 220 which, in turn, has a wired connection, over the Internet 240, with hospital or clinic 250 and a wireless connection with nearby caregiver 230. Activity monitor 216 would be either remotely commanded or internally pre-programmed to increase its sensitivity (i.e., lower its activity intensity thresholds) at certain predetermined time periods of interest (e.g., sundown and night time). In the preferred embodiment shown in FIG. 2, caregiver 230 carries a pager-like alarm device 235 which maintains the wireless connection with base station 220. Alarm device 235 is much less complex than DTR 120 or HHR 150 in the preferred embodiment of FIG. 1, and only alerts caregiver 230 when the activity intensity of patient 201 has reached what is believed to be a dangerous level. In a rest home embodiment such as FIG. 2, base station 220 may be in communication with activity monitors on multiple patients and, when an alert is given by alarm device 235 an identification code, number, or name is given so that caregiver 230 knows where to direct his or her attention.

There are many additional behavior monitoring programs and modification treatments possible using different embodiments of the present invention. Although the preferred embodiments described above are, in general, directed towards control of movement disorders, other embodiments may be used to treat sedentary non-movement or hypoactivity, rather than hyperactivity. In such embodiments, feedback and alarms would be generated when the activity intensity of the subject fell beneath a certain threshold. For example, in an embodiment which is used to modify a patient's caloric output by ensuring that the patient maintains a preset level of activity while exercising, different levels of feedback could be generated depending on how far below the preset level the patient's activity intensity has fallen. Besides caloric intake, embodiments treating hypoactivity could be used for subjects recovering from a cardiac incident or surgery, who are often required to maintain a certain activity level.

Low activity intensity detection would also be important for uses involving non-patients, such as sounding an alarm when periods of inattentiveness are noticed in personnel performing critical tasks (e.g., air traffic controllers, power plant operators, etc.). Knowledge of circadian cycles could be applied as well to heighten the activity monitor's sensitivity at periods of time when there is an increased likelihood of inattentiveness or sleep. This technology could also be applied to monitoring the attentiveness of long distance truck drivers and providing warnings when activity goes below a certain threshold.

Other embodiments of the present invention could be used as diagnostic tools. For instance, monitoring a subject's activity can be used to differentially diagnose bipolar disorder, as well as ADHD. Yet other embodiments of the present invention may be used to test the reaction time of a subject.

On the other hand, some embodiments of the present invention may be directed towards subjects other than human beings. For example, the same system and method could be applied to primate research. In such an embodiment, the components would behave in much the same manner, and feedback is used which is the most suitable for each species. In some cases, this may vary widely from what is found effective in humans.

Now that the depth of the present invention has been explored in reference to two preferred embodiments, and the breadth of the present invention has been explored by references to examples of alternate means, methods, and uses of the present invention, a conceptual model of the functional modules used to practice the present invention will be presented in FIG. 7.

FIG. 7 is a block diagram of the functional modules involved in activity monitoring according to various embodiments of the present invention. These functional modules are conceptual in nature, as their functionality may be carried out in one device, such as a microprocessor in an activity monitor, or parceled out among many devices, such as will be described in examples below. Furthermore, their manner of implementation is open to variation, as most functions could be performed by any of software (e.g., a program), firmware (e.g., as part of a device's operating system, stored in ROM-BIOS), or hardware (e.g., individual logic circuits and devices), as is well-known in the art. The functional modules on the inside of the dotted line in FIG. 7 are implemented inside the activity monitor in the preferred embodiment of FIG. 1. However, as will be discussed more fully below, the different functional modules may be implemented separately in one or more separate devices.

In FIG. 7, Motion Sensor 705 is shown connected to Network or Communication Bus (hereinafter referred to as "Network/Bus") 707. Although Network/Bus 707 is shown as a bus or network, its functionality could be implemented by other communication means, such as individual point-to-point communication links. In such an embodiment, Motion Sensor 705, for example, may have only two one-to-one communication links, one with Storage 710 and another with Epoch Feedback Unit 720. As mentioned above in relation to the preferred embodiment of FIG. 1, Motion Sensor 705 may take a wide variety of forms, including, but not limited to, solid state accelerometers, mercury switches, optical sensors, remote video sensors, and the specialized sensor discussed above which uses a pair of piezoelectric bimorph beams. In FIG. 7, movement measurements of subject human being 701 made by Motion Sensor 705 are communicated through Network/Bus 707 to Epoch Feedback Unit 720. In some embodiments, these movement measurements are also sent to be stored in Storage 710. This last feature allows the later download of raw data for a more thorough and complete analysis.

Epoch Feedback Unit 720 is comprised of Epoch Intensity Determination Means 723, Epoch Intensity-Threshold Comparator 725, and Epoch Feedback Signal Generator 727. The Epoch Intensity Determination Means 723, using movement measurements from either Motion Sensor 705 or Storage 710, determines the activity intensity at the end of each epoch. Epoch Intensity-Threshold Comparator 725 compares the determined activity intensity from Epoch Intensity Determination Means 723 to the epoch threshold, and generates a comparison result. The comparison result may take many forms, from a simple above/below signal to a more complicated signal indicating the magnitude and sign of the difference between the two values. In the preferred embodiment, the signal indicates the magnitude and sign. When the embodiment uses more than one level of threshold (e.g., primary and secondary), Epoch Intensity-Threshold Comparator 725 generates a more complicated result, which may indicate the determined activity intensity measurement's relationship with the nearest threshold, or all thresholds, etc. Epoch Feedback Signal Generator 727 receives the comparison result from Epoch Intensity-Threshold Comparator 725 and either generates or does not generate an epoch feedback signal based on the comparison result.

Although combined into one Epoch Feedback Unit 720 in the conceptual model of FIG. 7, Epoch Intensity Determination Means 723, Epoch Intensity-Threshold Comparator 725, and Epoch Feedback Signal Generator 727 could be implemented separately. For example, in an embodiment where the attached activity monitors are "dumb" (lacking processing and memory resources) and the remote DTR is "smart", the Epoch Intensity Determination Means 723 may be implemented as simple circuitry in the attached activity monitor, which transmits the determined activity intensity value to the DTR, and the Epoch Intensity-Threshold Comparator 725 may be implemented by one or more processing units in the DTR, in which the transmitted activity intensity values are continually stored, processed, and analyzed. Based on this processing and analysis, the DTR may or may not generate a feedback signal. This feedback signal is transmitted to the activity monitor, which would then generate feedback.

In the preferred embodiment, a microprocessor in the activity monitor performs the functions of Epoch Feedback Unit 720. However, in other embodiments, electric circuits could perform these functions. For example, while Motion Sensor 705 is continually outputting a movement measurement as a voltage, an integrator circuit could trap that voltage over time in a capacitor, and then a comparator circuit could compare the accumulated voltage to a reference voltage (representing the epoch threshold) at the end of each epoch, when the accumulated voltage is discharged. Furthermore, in the preferred embodiment, the activity monitor microprocessor commands, or does not command, the vibratory motor in the activity monitor to vibrate based on the result of comparing the determined epoch activity intensity to the epoch threshold. Similarly, in the conceptual model of FIG. 7, Epoch Feedback Signal Generator 727 sends, or does not send, an epoch feedback signal to the Epoch Feedback Output 750 based on the comparison result generated by Epoch Intensity-Threshold Comparator 725. Epoch Feedback Output 750 generates output which operates as behavioral modification feedback for subject human being 701.

Session Feedback Unit 730 is comprised of Session Intensity Determination Means 733, Session Intensity-Threshold Comparator 735, and Session Feedback Signal Generator 737. The Session Intensity Determination Means 733, using past determined epoch intensity values, determines the current session intensity by taking an average of the past determined epoch intensity values. The past determined epoch intensity values, having been generated by Epoch Intensity Determination Means 723, may be stored in Storage 710, from which the Session Intensity Determination Means 733 retrieves them in order to determine the session intensity. As with the other functional modules, it is possible to integrate this aspect of Storage 710's functionality into Session Feedback Unit 730, in which case determined epoch intensity values would be directly outputted to Session Feedback Unit 730.

Although session intensity is defined here as an average of stored epoch intensity values, it is possible to define session intensity in other ways. Session Intensity-Threshold Comparator 735 compares the determined session intensity from Session Intensity Determination Means 733 to the session threshold, and generates a comparison result. As with the epoch intensity, the comparison result may take many forms, and it is possible to have multiple thresholds. In the preferred embodiment, the comparison result indicates where the session intensity falls in relation to the primary and secondary thresholds. Session Feedback Signal Generator 737 receives the comparison result from Session Intensity-Threshold Comparator 735 and either generates or does not generate a session feedback signal based on the comparison result. In the preferred embodiment, session intensity is determined when the subject human being 701 indicates through Subject Input 780 that he or she wants to see the current session intensity value. In addition, session intensity is automatically determined at the end of the session. Session Feedback Signal Generator 737 sends a session feedback signal to the Session Feedback Output 760 based on the comparison result generated by Session Intensity-Threshold Comparator 735. Session Feedback Output 760 generates output which operates as behavioral modification feedback for subject human being 701. In the preferred embodiment discussed above, this generated output was in the form of 3 LEDs on the activity monitor.

Communication Link 740 is used to download information to, and upload commands from, Base Station 790. Base Station 790 may be the HHR, the DTR, a PC for performing analysis, etc. Communication Link 740 may be a wired or wireless, networked or point-to-point connection. In some embodiments, Base Station 790 may only upload commands; in other embodiments, Base Station 790 may only download information. There may be multiple Base Station 790s. The information that might be downloaded to Base Station 790 includes, but is not limited to, movement measurements, determined epoch or session intensity values, epoch or session feedback signals, and subject input. Commands that might be uploaded from Base Station 790 include, but are not limited to, start, stop, or reset session, change epoch or session threshold(s) to another certain value(s), change epoch or session threshold(s) by a relative amount (such as a percentage), and control feedback to subject 701.

Base Station 790 includes an Input module 792, an Analysis (or processing) module 794, a Storage module 796, and an Output module 798. Human supervisor 799 controls the Base Station 790 and one or more activity monitors through Input 792, and receives downloaded information and analyses of downloaded information through Output 798. Human supervisor 799 may or may not be performing these acts simultaneously with the activity monitoring. For example, the attached activity monitor may run during the entire session without having Communication Link 740, then, after the session is over, the activity monitor is connected to the Base Station 790. At this time, human supervisor 799 downloads, stores, and analyzes information collected by the activity monitor. In addition, human supervisor 799 may change operating parameters of the activity monitor, such as thresholds, length of epochs, etc. In some embodiments, these functions may be automated so that there is no human supervisor 799 at all. In such embodiments, human involvement may not consist of "monitoring", but of higher-level analysis, i.e., interpretation of analyzed and collated data.

As mentioned above in relation to "dumb" activity monitors and "smart" DTRs, the functional modules of conceptual model FIG. 7 may migrate, combine, or divide. Individual functional modules may be implemented as stand alone devices separate from the other devices. For instance, one of the feedback units could be implemented as a separate device. Some of the modules that are shown having a communication link with Base Station 790 may migrate to Base Station 790. Similarly, some of the modules shown in Base Station 790 may migrate to the activity monitor. Even the feedback output to subject 701 could migrate. The feedback might be displayed at a centralized point for group consumption. Although this is not preferable in a classroom environment, a highly visible board displaying each subject's activity intensity might be useful in an air traffic control room, an occupational therapy clinic, or the dispatch office of a trucking company (this last one would not necessarily be visible to the subjects).

An example of combination would be an embodiment where a single digital signal processing (DSP) chip is used to perform the functions of both feedback units 720 and 730. As an example of separation, Motion Sensor 705 may be separated into many modules or have additional modules for pre-processing. For example, if multiple sensor patches are placed at different points on subject 701's body, the data produced by them may need to be combined and smoothed, or undergo other sorts of signal processing.

Besides epoch and session, other time periods might be utilized when defining thresholds in other embodiments. In such embodiments, there would be additional feedback units, and perhaps additional feedback output to subject 701.

In the preferred embodiment, the activity monitor microprocessor acts as a controller for most of the functions shown in FIG. 7. However, a controller is not shown in FIG. 7, as it is not necessary to coordinate the functional modules in every embodiment of the present invention. Indeed, each module may operate independently of each other, or all of the modules may be performed by a specially designed application specific integrated circuit (ASIC) chip.

Having discussed embodiments of the present invention in reference to an abstract conceptual model, we will now present results of an actual experimental embodiment of the present invention with reference to FIGS. 5A, 5B, and 6A–6I.

Figure 5B:
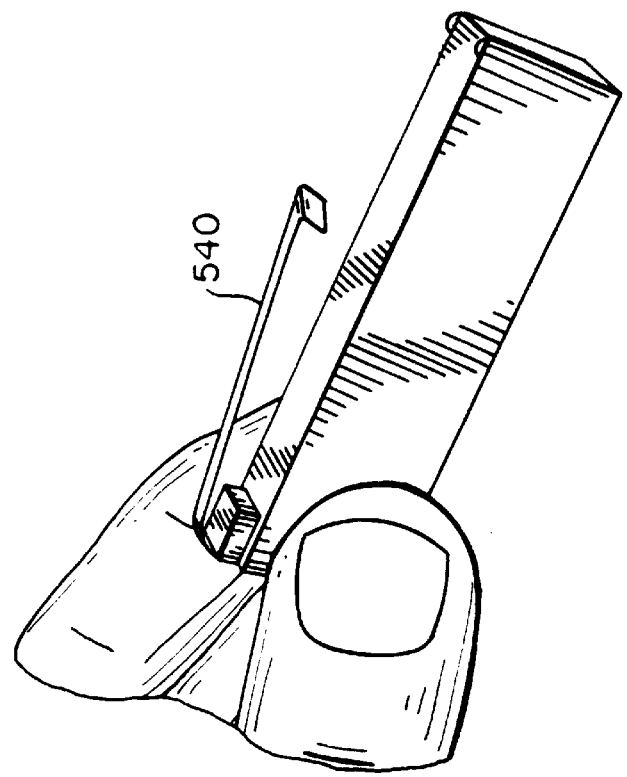
FIGS. 5A and 5B are front and side views, respectively, of an experimental activity monitor according to an embodiment of the present invention.
Figure 5A:
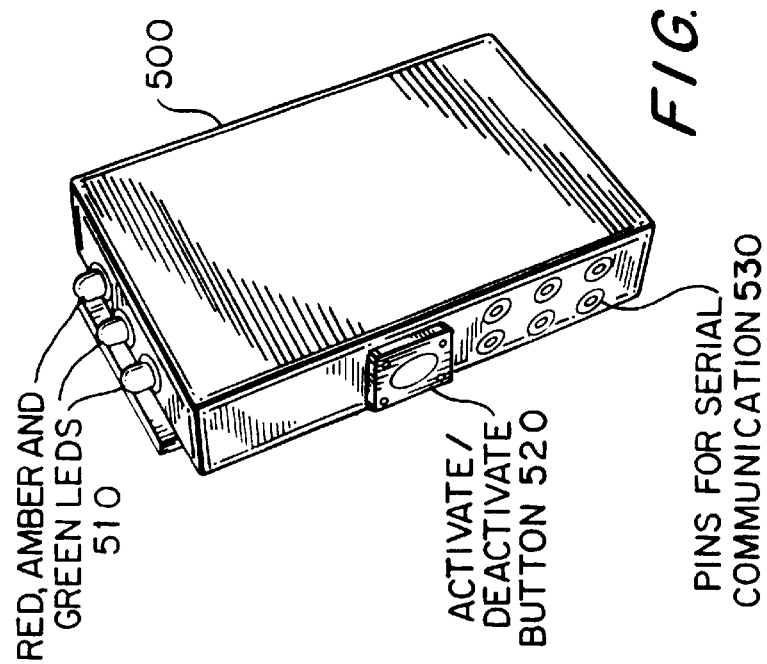

In experiments employing an embodiment of the present invention, results showed clear evidence of effectiveness. In these experiments, an activity monitor 500 (as shown in FIGS. 5A and 5B) which is similar in weight and size to a pager was used. Activity monitor 500 measures 2.75×0.625 v 1.69 inches, weighs 2.5 ounces, and uses a ½ AA battery as a power source. As shown in the view of FIG. 5A, experimental activity monitor 500 has red, amber, and green LEDs 510 on its top, with an ON/OFF button 520 and pins 530 for serial communication located on its side. Instead of wireless data retrieval and telemetry, this experimental embodiment used serial pins 530 to download collected activity data to a desktop computer with an appropriate interface As shown in the view of FIG. 5B, experimental activity monitor 500 used a belt clip 540 to clip to material, such as a belt, at the waist of the monitored children. A piezoelectric sensor was used to generate activity data, which was sampled at a rate of 10 Hz. The activity data was filtered at the 2–3 Hz range with a sensitivity of 0.02 g (or gravity, a unit for measuring acceleration) at the midband. Activity monitor 500's on-board data storage is 32K of flash memory, which retains recorded data even when activity monitor 500 is turned off. Data starts being stored after ON/OFF button 520 has been pressed continuously for a period of five or more seconds.

The results of the first series of experiments indicated what was shown above in reference to FIGS. 4A and 4B;

namely, that a ZC count is an inadequate measure of hyperactivity and that a PIM measure of intensity is much better suited to the task. In a second series of experiments, the PIM measure was used. Furthermore, the problem of vibrotactile feedback generated by the activity monitor causing inaccurate data results was indicated in the first series of experiments. In the second series of experiments, two activity monitors were used, so that, when the first activity monitor was generating vibrotactile feedback and, thus, recording inaccurate data, the second activity monitor would be recording accurate data.

In the second series of experiments, nine children (8 boys and 1 girl, mean age 8.6 years, with an age range of 8–9 years old) out of a class of approximately 12 children participated. All of the nine students were diagnosed with ADHD, and, while medicated, still demonstrated motor excess. Session lengths were shorter than planned, approximately 20 to 25 minutes, and epoch lengths were 5 seconds.

Between 3 and 4 baseline readings (with no feedback) were collected at the beginning of the series, from which mean activity levels and standard deviations were calculated. The experiment used the primary and secondary, instantaneous (or epoch) and session thresholds as discussed above. The primary epoch threshold was the mean baseline activity level, the secondary epoch threshold was set at the mean plus two standard deviations, thus allowing a large dynamic range over which to provide feedback. Exceeding the primary epoch threshold caused a vibrotactile pulse of 0.5 seconds, with the vibrotactile pulses increasing proportionally and stepwise in length of time as the amount of activity intensity exceeding the primary epoch threshold. If the activity intensity reached the secondary epoch threshold, a maximum vibrotactile pulse of 5 seconds was generated.

The primary session threshold was set at approximately 20% below the baseline mean. Unlike the preferred embodiment of FIG. 1, the secondary session threshold was set at one standard deviation above the baseline mean so that most children would receive some recognition, e.g. a partial award. It was contemplated that, for long-time use, the thresholds would be lowered, over time, for subsequent sessions. When below the primary session threshold, the green LED lit; when between the primary threshold and the secondary threshold, the amber LED lit; and, when above the secondary threshold, the red LED lit. At the end of the session, children with a green LED lit would receive full rewards, children with an amber LED lit would receive a partial reward, and children with a red LED lit would receive nothing. Rewards were given from two "grab bags" of prizes. The first bag contained full rewards consisting of small toys valued at less than $5, and the second bag held partial rewards, consisting of smaller items, such as colorful stickers. The children were allowed to examine the contents of the bag, before putting their hands into the closed bag to retrieve their reward.

The results of the second series of experiments for each of the nine subjects are shown in FIGS. 6A through 6I. As shown in FIGS. 6A through 6I, six of the nine subjects showed clear evidence of effectiveness, two subjects showed some evidence of effectiveness, and one subject showed no evidence of effectiveness. In the each graph, there are two horizontal lines: an upper line (labelled "Red LED") corresponding to the secondary session threshold established for that particular subject, and a lower line (labelled "Amber LED") corresponding to the primary session threshold established for that subject. The left-hand side of each graph represents the baseline readings, and the right-hand side represents the feedback readings taken at the end of individual sessions.

Figure 6A:
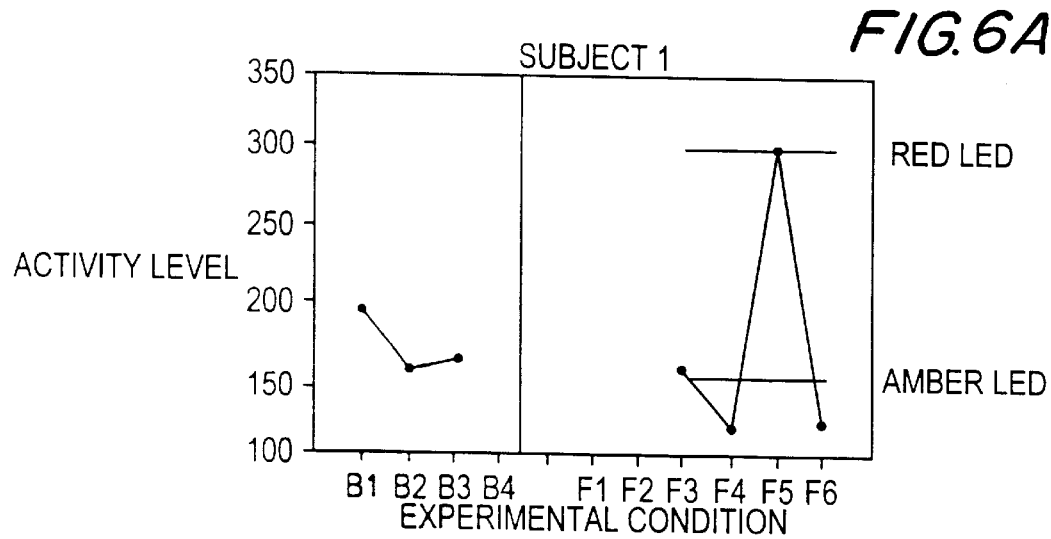
FIGS. 6A through 6I are graphical presentations of the results of an experiment on nine test subjects using the experimental activity monitor of FIGS. 5A and 5B, according to an embodiment of the present invention.
Figure 6B:
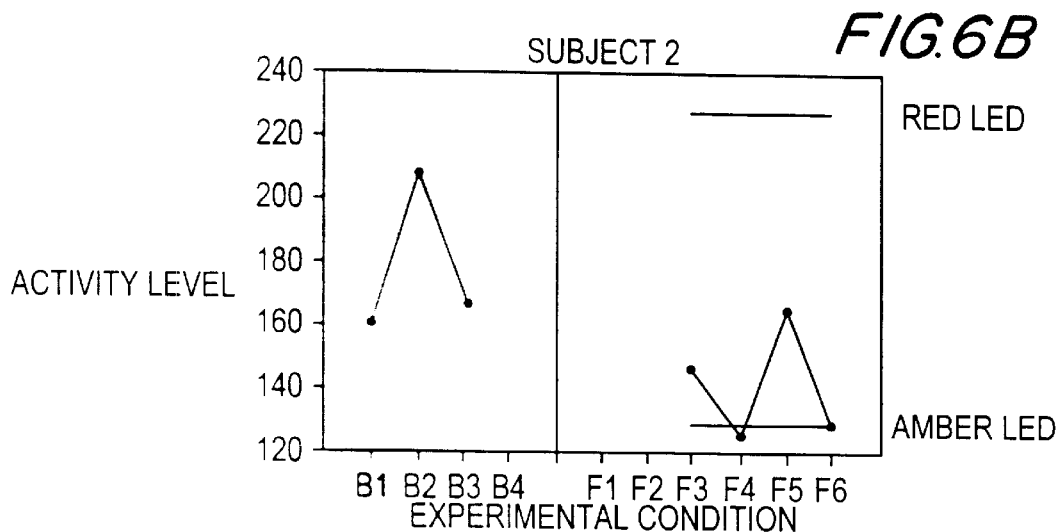
Figure 6C:
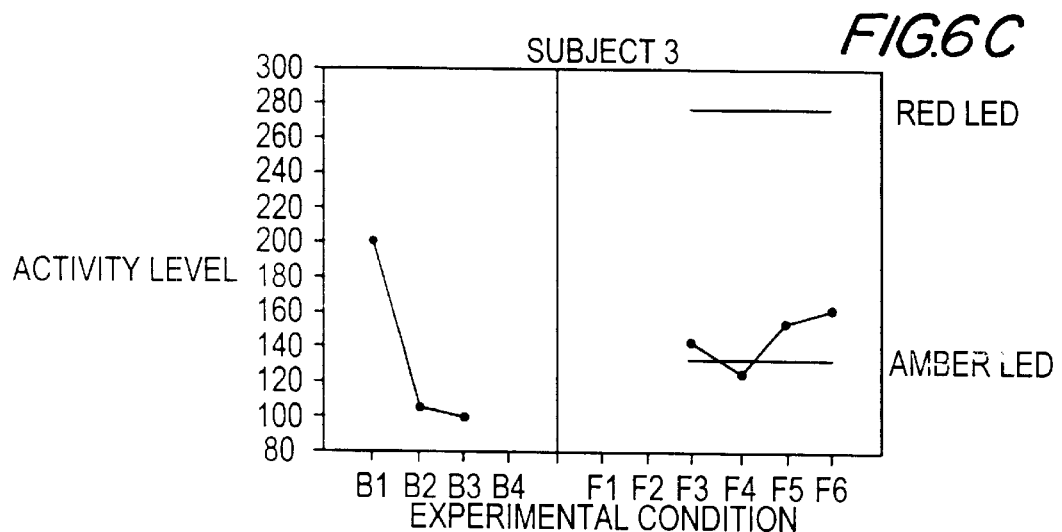
Figure 6D:
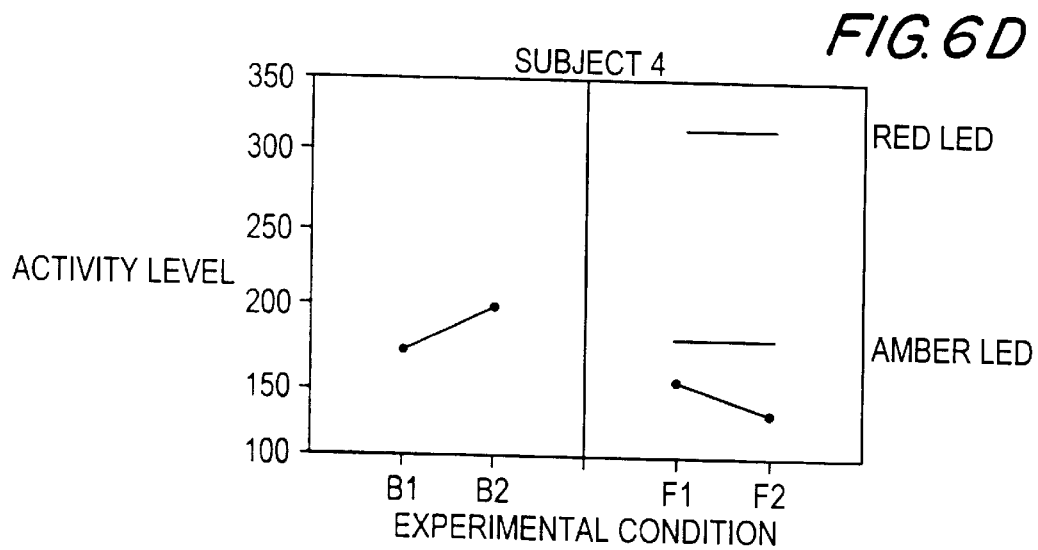
Figure 6E:
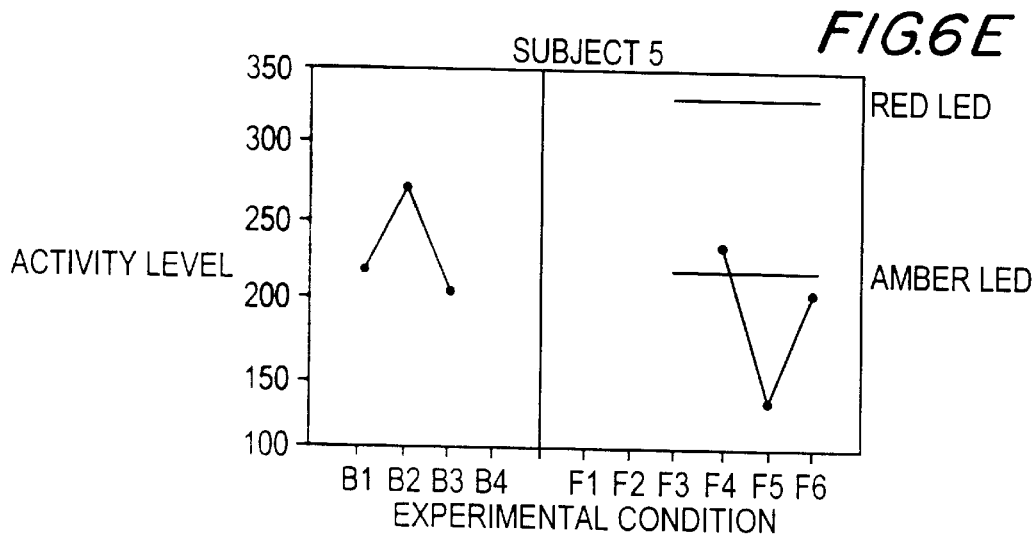
Figure 6F:
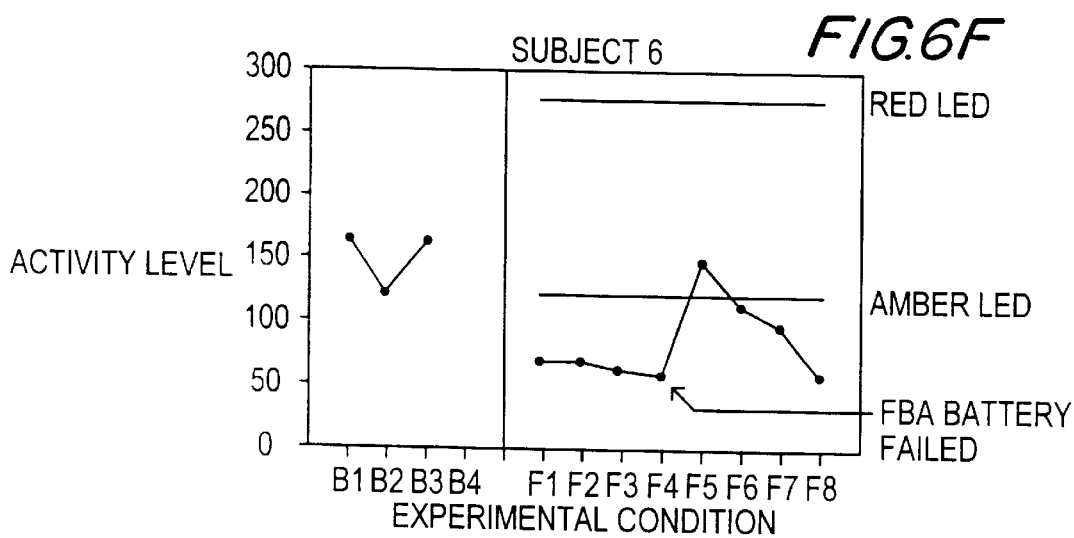
Figure 6G:
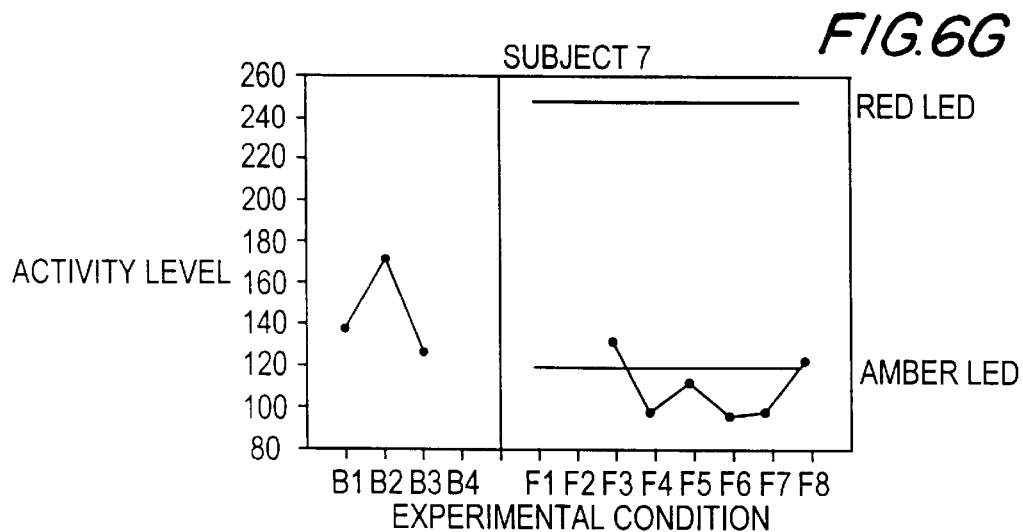
Figure 6H:
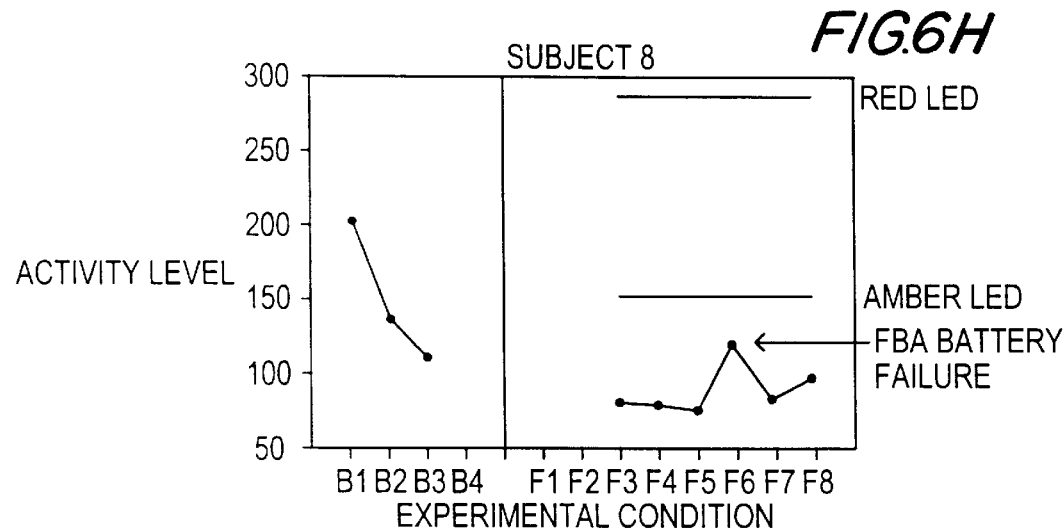
Figure 6I:
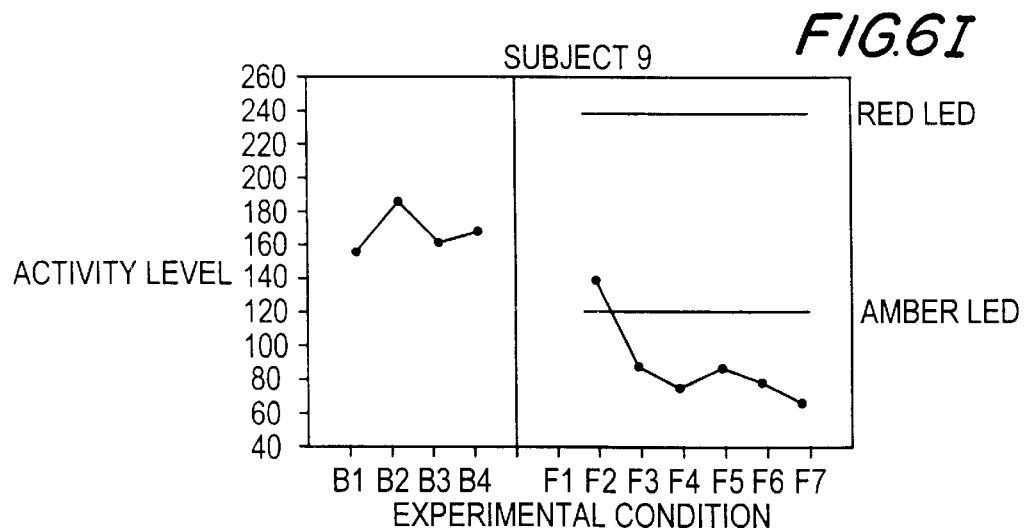

Clear evidence of effectiveness was shown by subject 2 (FIG. 6B), subject 4 (FIG. 6D), and subject 9 (FIG. 6I). Good evidence of effectiveness was shown by subject 5 (FIG. 6E), subject 6 (FIG. 6F), and subject 7 (FIG. 6G). Partial evidence of effectiveness was shown by subject 1 (FIG. 6A) and subject 8 (FIG. 6H). Evidence of ineffectiveness was shown in subject 3 (FIG. 6C).

Subject 2 (FIG. 6B) shows clear evidence of effectiveness because three of four feedback values (F3, F4, and F6) are below the lowest baseline value (B1), and two feedback values (F4 and F6) are below the primary session threshold. Subjects 4 (FIG. 6D) and 9 (FIG. 6I) show clear evidence of effectiveness for the same reason: all feedback values are below the lowest baseline value.

Subject 5 (FIG. 6E) show good evidence of effectiveness because two of the feedback values (F4 and F5) are lower than all three baseline values. Similarly, subject 6 (FIG. 6F) shows good evidence of effectiveness because the first four feedback points (F1–F4) are below all three baseline values. In addition, all feedback values except one (F5) are below the primary session threshold. Subject 7 (FIG. 6G) shows good evidence of effectiveness in that all but the first feedback point (F3) are below the primary threshold.

Subject 1 (FIG. 6A) shows partial evidence of effectiveness was shown by the fact that two feedback values (F4 and F6) are below the three baseline values. Subject 8 (FIG. 6H) shows similar partial evidence because all but one feedback value (F6) were below all three baseline values.

Subject 3 shows evidence of ineffectiveness because all but one feedback value (F4) are above the primary threshold, and all of the feedback values are above two of the baseline values (B2 and B3).

In the experimental embodiment, a small, unobtrusive pager-like device was designed and tested. In the experiments, the children found the devices comfortable and not encumbering: they wore the devices without problem or incident. They showed no reluctance to wear the devices and were not teased or embarrassed by other children. The devices were found compatible with classroom practice. The positive results as described above reinforce the concept that activity levels of subjects cab reduced using both contingent feedback and positive reinforcement.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of modifying an activity level of a subject, said subject being one of a human being and a primate, comprising the steps of:

detecting a level of physical movement of a subject;
   measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

determining whether an epoch intensity measurement crosses an epoch threshold;

sending, if the epoch intensity measurement crosses the epoch threshold, an epoch feedback signal to one of the subject, a supervisor, and both the subject and the supervisor, where said epoch feedback signal is proportional to an amount that the epoch intensity measurement crosses the epoch threshold;

recording the epoch intensity measurement at the end of each epoch; and calculating a session intensity measurement based on the recorded epoch intensity measurements.

2. The activity level modification method of claim 1, wherein the detecting a level of physical movement of a subject comprises:

detecting a level of acceleration of the subject.

3. The activity level modification method of claim 1, wherein the step of detecting the level of physical movement of the subject is performed by a motion sensor in an activity monitor which is physically attached to the subject.

4. The activity level modification method of claim 3, wherein the motion sensor comprises one of a solid state accelerometer, a mercury switch, an optical sensor, and a pair of piezoelectric bimorph beams.

5. The activity level modification method of claim 1, wherein the epoch intensity measurement crosses the epoch threshold by one of being greater than the epoch threshold and being less than the epoch threshold.

6. A method of modifying an activity level of a subject, said subject being one of a human being and a primate, comprising the steps of:

detecting a level of physical movement of a subject;

measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

determining whether an epoch intensity measurement crosses an epoch threshold; and sending, if the epoch intensity measurement crosses the epoch threshold, an epoch feedback signal to one of a subject, a supervisor, and both the subject and the supervisor, where said epoch feedback signal is proportional to an amount that the epoch intensity measurement crosses the epoch threshold;

wherein the intensity of physical movement in a graph of the detected of the detected level of physical movement over time is defined by a line in the graph representing a physical movement threshold and a line in the graph representing the detected level of physical movement.

7. The activity level modification method of claim 6, wherein the line representing the detected level of physical movement on the graph of the detected level of physical movement over time is rectified.

8. The activity level modification method of claim 6, wherein the intensity of physical movement is defined as an integration of an area between the line representing a physical movement threshold and the line representing the detected level of physical movement on the graph of the detected level of physical movement over time, wherein the epoch threshold is a predetermined quantity of integrated area per epoch.

9. The activity level modification method of claim 6, wherein the intensity of physical movement is defined as a number of times the line representing the detected level of physical movement crosses the line representing a physical movement threshold on the graph of the detected level of physical movement over time, wherein the epoch threshold is a predetermined number of line crossings per epoch.

10. The activity level modification method of claim 6, wherein the intensity of physical movement is defined as an amount of time the line representing the detected level of physical movement is one of above and below the line representing a physical movement threshold on the graph of the detected level of physical movement over time, wherein the epoch threshold is a predetermined period of time per epoch.

11. The activity level modification method of claim 1, wherein the calculating the session intensity measurement comprises the step of:

calculating a session intensity measurement from an average of recorded epoch intensity measurements.

12. The activity level modification method of claim 1, further comprising the step of:

determining the relationship of the calculated session intensity measurement to a session threshold.

13. The activity level modification method of claim 12, wherein the determined relationship of the calculated session intensity measurement to the session threshold is one of an amount by which the calculated session intensity measurement is in excess of the session threshold and an amount by which the calculated session intensity measurement is short of the session threshold.

14. The activity level modification method of claim 12, further comprising the step of:

sending, if the session intensity measurement crosses a session threshold, a session feedback signal to one of the subject, a supervisor, and both the subject and the supervisor.

15. The activity level modification method of claim 12, further comprising the step of:

sending a session feedback signal to one of the subject, a supervisor, and both the subject and the supervisor, where said session feedback signal is proportional to the determined relationship of the calculated session intensity measurement to the session threshold.

16. The activity level modification method of claim 1, wherein the step of calculating a session intensity measurement is performed when a session intensity measurement request is received.

17. The activity level modification method of claim 16, wherein the session intensity measurement request is generated by input from one of the subject and a supervisor.

18. The activity level modification method of claim 1, wherein the epoch feedback signal comprises one of vibrotactile feedback, audio feedback, and visual feedback.

19. The activity level modification method of claim 1, wherein one of a length of time of the epoch feedback signal and an amplitude of the epoch feedback signal is proportional to the amount that the epoch intensity measurement crosses the epoch threshold.

20. The activity level modification method of claim 1, wherein, before the determining and sending steps, said method further comprises the steps of:

measuring the intensity of physical movement of the subject human being over at least one epoch;

recording the measured intensity of physical movement of the subject human being at the end of each epoch of the at least one epoch;

calculating an average intensity of physical movement of the subject human being, said average intensity of physical movement being an average of the recorded measured intensities; and setting the epoch threshold equal to the calculated average intensity.

21. A system for modifying an activity level of a subject, said subject being one of a human being and a primate, comprising:

a motion sensor for detecting a level of physical movement of a subject;

means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

means for determining whether an epoch intensity measurement crosses an epoch threshold;

means for sending, if the epoch intensity measurement crosses the epoch threshold, an epoch feedback signal to one of the subject, a supervisor, and both the subject and the supervisor, where said epoch feedback signal is proportional to an amount that the epoch intensity measurement crosses the epoch threshold;

means for recording the epoch intensity measurement at the end of each epoch; and means for calculating a session intensity measurement based on recorded epoch intensity measurements.

22. The activity level modification system of claim 21, further comprising:

an activity monitor which is physically attached to the subject, said activity monitor comprising said motion sensor.

23. The activity level modification system of claim 21, wherein said motion sensor comprises:

a pair of piezoelectric bimorph beams.

24. The activity level modification system of claim 21, wherein said motion sensor comprises one of a solid state accelerometer, a mercury switch, and an optical sensor.

25. The activity level modification system of claim 21, further comprising:

means for recording the detected level of physical movement.

26. The activity level modification system of claim 21, wherein the means for calculating a session intensity measurement comprises:

means for calculating a session intensity measurement as an average of recorded epoch intensity measurements.

27. The activity level modification system of claim 21, further comprising:

means for determining the relationship of the session intensity measurement to a session threshold.

28. The activity level modification system of claim 27, wherein the means of determining the relationship of the session intensity measurement to a session threshold further comprises:

means for determining whether the session intensity measurement crosses a session threshold.

29. The activity level modification system of claim 21, further comprising:

means for sending a session feedback signal to one of the subject, a supervisor, and both the subject and the supervisor.

30. The activity level modification system of claim 27, wherein the session feedback signal is proportional to the determined relationship of the session intensity measurement to a session threshold.

31. The activity level modification system of claim 21, further comprising:

a session feedback means for receiving a session measurement request from the subject and for generating a session feedback signal to the subject, said session feedback signal corresponding to the calculated session intensity measurement.

32. The activity level modification system of claim 31, wherein the session feedback means comprises:

means for calculating a session intensity measurement as an average of recorded epoch intensity measurements;

means for determining the difference between the calculated session intensity measurement and a session threshold and for determining whether the calculated session intensity measurement is less than or greater than the session threshold; and means for sending a session feedback signal to the subject human being, where said session feedback signal corresponds to a magnitude of the determined difference and whether the calculated session intensity measurement is less than or greater than the session threshold.

33. The activity level modification system of claim 21, wherein the epoch feedback signal comprises one of vibrotactile feedback, audio feedback, and visual feedback.

34. The activity level modification system of claim 21, wherein one of a length of time of the epoch feedback signal and an amplitude of the epoch feedback signal is proportional to the amount that the epoch intensity measurement crosses the epoch threshold.

35. The activity level modification system of claim 21, further comprising:

means for setting the epoch threshold, said means comprising means for measuring the intensity of physical movement of the subject over at least one epoch;

means for recording the measured intensity of physical movement of the subject at the end of each epoch of the at least one epoch;

means for calculating an average intensity of physical movement of the subject, said average intensity of physical movement being an average of the recorded measured intensities; and means for setting the epoch threshold equal to the calculated average intensity.

36. A system for modifying an activity level of a subject, said subject being one of a human being and a primate, comprising:

a motion sensor for detecting a level of physical movement of a subject;

an epoch feedback unit comprising:

means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

means for determining whether an epoch intensity measurement crosses an epoch threshold; and epoch feedback signal means for generating, if the epoch intensity measurement crosses the epoch threshold, an epoch feedback signal, where said epoch feedback signal is proportional to an amount that the epoch intensity measurement crosses the epoch threshold; and a session feedback unit comprising:

means for recording the epoch intensity measurement at the end of each epoch;

means for calculating a session intensity measurement from an average of recorded epoch intensity measurements;

means for determining whether the session intensity measurement crosses a session threshold; and session feedback signal means for generating a session feedback signal, where said epoch feedback signal is proportional to an amount that the session intensity measurement crosses the session threshold.

37. The activity level modification system of claim 36, further comprising:

an activity monitor attached to the subject, said activity monitor comprising said motion sensor, said epoch feedback unit, said session feedback unit, and further comprising:

means for producing epoch feedback which is apprehended by the subject, said epoch feedback being generated from an epoch feedback signal;

means for producing session feedback which is apprehended by the subject, said session feedback being generated from a session feedback signal.

38. The activity level modification system of claim 37, wherein the means for producing epoch feedback comprises one of a display means for generating a visual display, a vibrating means for generating vibrotactile feedback, and an audio means for generating audio feedback.

39. The activity level modification system of claim 37 wherein the means for producing session feedback comprises one of a display means for generating a visual display, a vibrating means for generating vibrotactile feedback, and an audio means for generating audio feedback.

40. The activity level modification system of claim 36, wherein one of a length of time of the epoch feedback signal and an amplitude of the epoch feedback signal is proportional to the amount that the epoch intensity measurement crosses the epoch threshold.

41. The activity level modification system of claim 38, wherein the vibrating means receives a generated epoch feedback signal and generates a vibrotactile signal, where one of a length of time of said vibrotactile signal and an amplitude of said vibrotactile signal is proportional to the amount that the epoch intensity measurement crosses the epoch threshold.

42. The activity level modification system of claim 39, wherein the display means comprises a Liquid Crystal Display (LCD) and wherein the generated visual display uses one of icons, numerals, images, and words to represent the amount that the session intensity measurement crosses the session threshold.

43. The activity level modification system of claim 39, wherein the display means comprises at least one Light Emitting Diode (LED) and wherein the generated visual display uses one of color, luminosity, a number of lit LEDs of a plurality of said at least one LED, and a location of at least one lit LED of said at least one LED to represent the amount that the session intensity measurement crosses the session threshold.

44. The activity level modification system of claim 37, further comprising:

a communication link between an activity monitor and a base station;

said activity monitor attached to the subject, the activity monitor comprising:

means for establishing a connection to the communication link; and a base station for downloading information from a group of activity monitors, said group of activity monitors comprising at least said activity monitor attached to the subject, the base station comprising:

means for establishing a connection with the communication link.

45. The activity level modification system of claim 44, wherein the base station further comprises:

means for output of said downloaded information, where said output may be apprehended by a supervisor.

46. The activity level modification system of claim 44, wherein the base station further comprises:

means for receiving input from a supervisor.

47. The activity level modification system of claim 44, wherein the communication link comprises a wireless communication link, wherein the connection establishment means of the activity monitor comprises one of a wireless transmitter and a wireless transceiver, and wherein the connection establishment means of the base station comprises one of a wireless receiver and a wireless transceiver.

48. The activity level modification system of claim 44, wherein the communication link comprises a wire communication link, said wire communication link comprising one of a network and a direct wire connection between connection establishment means of the activity monitor and the connection establishment means of the base station.

49. The activity level modification system of claim 44, wherein the base station comprises one of a hand-held unit and a desk-top unit.

50. The activity level modification system of claim 44, wherein the base station comprises a personal computer (PC).

51. The activity level modification system of claim 44, wherein the base station further comprises:

means for controlling an activity monitor.

52. The activity level modification system of claim 45, wherein the means for output of said downloaded information means comprises one of a vibrotactile output means, an audio output means, and a visual output means.

53. The activity level modification system of claim 45, wherein the visual output means comprises one of a cathode ray tube (CRT), a plasma display screen, at least one Light Emitting Diode (LED), a touchscreen, and a Liquid Crystal Display (LCD).

54. The activity level modification system of claim 53, wherein the visual output means comprises at least one LED, and the generated visual display uses one of color, luminosity, a number of lit LEDs of a plurality of said at least one LED, and a location of at least one lit LED of said at least one LED.

55. The activity level modification system of claim 53, wherein the visual output means comprises a Liquid Crystal Display (LCD) and wherein the generated visual display uses one of icons, numerals, images, and words to represent the amount that the session intensity measurement crosses the session threshold.

56. A method of modifying an activity level of a subject, said subject being one of a human being and a primate, comprising the steps of:

detecting a level of physical movement of a subject;

searching for a match between the detected level of physical movement and a predetermined pattern of physical movement;

sending, if there is a match between the detected level of physical movement and the predetermined pattern of physical movement, a pattern recognition feedback signal to one of the subject, a supervisor, and both the subject and the supervisor;

recording a number of times a pattern recognition feedback signal is sent during an epoch, wherein said epoch is a predetermined period of time which is continuously repeated;

determining, at an end of each epoch, whether the recorded number of times a pattern recognition feedback signal was sent during the epoch which ended crosses an epoch threshold; and sending, if the recorded number of times a pattern recognition feedback signal was sent during the epoch which ended crosses the epoch threshold, an epoch feedback signal to the subject, where said epoch feedback signal is proportional to an amount that the recorded number of times a pattern recognition feedback signal was sent during the epoch which ended crosses the epoch threshold.

57. The activity level modification method of claim 56, wherein the detecting the level of physical movement of the subject comprises:

detecting a level of acceleration of the subject.

58. A method of modifying an activity level of a subject, said subject being one of a human being and a primate, comprising the steps of:

detecting a level of physical movement of an object;

recording the detected level of physical movement;

searching for a match between the detected level of physical movement and a predetermined pattern of physical movement by maintaining a sliding window of analysis, wherein said sliding window is a time period over which the recorded detected level of physical movement is searched for the predetermined pattern of physical movement, said sliding window sliding forward in time; and sending, if there is a match between the detected level of physical movement and the predetermined pattern of physical movement, a pattern recognition feedback signal to one of a subject, a supervisor, and both the subject and the supervisor.

59. A method of modifying an activity level of a subject, said subject being one of a human being and a primate, comprising the steps of:

detecting a level of physical movement of a subject;

measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

determining whether an epoch intensity measurement crosses an epoch threshold;

sending, if the epoch intensity measurement crosses the epoch threshold, an epoch feedback signal to one of the subject, a supervisor, and both the subject and the supervisor;

wherein the epoch threshold is set by performing the steps of:

measuring the intensity of physical movement of the subject human being over at least one epoch;

recording the measured intensity of physical movement of the subject human being at the end of each epoch of the at least one epoch;

calculating an average intensity of physical movement of the subject human being, said average intensity of physical movement being an average of the recorded measured intensities; and setting the epoch threshold equal to the calculated average intensity.

60. A system for modifying an activity level of a subject, said subject being one of a human being and a primate, comprising:

a motion sensor for detecting a level of physical movement of a subject, said motion sensor comprising a pair of piezoelectric bimorph beams;

means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

means for determining whether an epoch intensity measurement crosses an epoch threshold; and means for sending, if the epoch intensity measurement crosses the epoch threshold, an epoch feedback signal to one of the subject, a supervisor, and both the subject and the supervisor, where said epoch feedback signal is proportional to an amount that the epoch intensity measurement crosses the epoch threshold.

61. A system for modifying an activity level of a subject, said subject being one of a human being and a primate, comprising:

a motion sensor for detecting a level of physical movement of a subject;

means for measuring an intensity of physical movement of the subject, said intensity of physical movement being based on the detected level of physical movement, said measuring beginning at the start of, and being reset at the end of, an epoch, such that a measurement of intensity is produced for each epoch, wherein said epoch is a predetermined period of time which is continuously repeated;

means for determining whether an epoch intensity measurement crosses an epoch threshold;

means for sending, if the epoch intensity measurement crosses the epoch threshold, an epoch feedback signal to one of the subject, a supervisor, and both the subject and the supervisor, where said epoch feedback signal is proportional to an amount that the epoch intensity measurement crosses the epoch threshold; and means for setting the epoch threshold, said means comprising:

means for measuring the intensity of physical movement of the subject over at least one epoch;

means for recording the measured intensity of physical movement of the subject at the end of each epoch of the at least one epoch;

means for calculating an average intensity of physical movement of the subject, said average intensity of physical movement being an average of the recorded measured intensities; and means for setting the epoch threshold equal to the calculated average intensity.

62. The activity level modification method of claim 58, wherein the detecting the level of physical movement of the subject comprises:

detecting a level of acceleration of the subject.

* * * * *